US011712188B2

(12) United States Patent
Ghosh

(10) Patent No.: US 11,712,188 B2
(45) Date of Patent: Aug. 1, 2023

(54) POSTERIOR LEFT BUNDLE BRANCH ENGAGEMENT

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 475 days.

(21) Appl. No.: 16/815,133

(22) Filed: Mar. 11, 2020

(65) Prior Publication Data

US 2020/0352470 A1 Nov. 12, 2020

Related U.S. Application Data

(60) Provisional application No. 62/844,513, filed on May 7, 2019.

(51) Int. Cl.
| | | |
|---|---|---|
| *A61N 1/368* | (2006.01) | |
| *A61B 5/282* | (2021.01) | |
| *G16H 50/30* | (2018.01) | |
| *G16H 50/20* | (2018.01) | |
| *A61N 1/37* | (2006.01) | |

(52) U.S. Cl.
CPC ............ *A61B 5/282* (2021.01); *A61N 1/368* (2013.01); *A61N 1/371* (2013.01); *G16H 50/20* (2018.01); *G16H 50/30* (2018.01); *A61B 2562/043* (2013.01)

(58) Field of Classification Search
CPC .. A61N 1/371; A61N 1/368; A61B 2562/043; A61B 5/282; G16H 50/30; G16H 50/20
See application file for complete search history.

(56) References Cited

U.S. PATENT DOCUMENTS

| | | |
|---|---|---|
| 3,835,864 A | 9/1974 | Rasor et al. |
| 3,865,118 A | 2/1975 | Bures |
| 3,943,936 A | 3/1976 | Rasor et al. |
| 3,949,757 A | 4/1976 | Sabel |
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Mass |

(Continued)

FOREIGN PATENT DOCUMENTS

| | | |
|---|---|---|
| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Allen Porter
*Assistant Examiner* — Skylar Lindsey Christianson
(74) *Attorney, Agent, or Firm* — Mueting Raasch Group

(57) ABSTRACT

Systems and methods may monitor electrical activity of a patient's heart using electrodes during delivery of cardiac therapy and determine a degree of posterior left bundle branch engagement based on the monitored electrical activity. The systems and methods may adjust the cardiac therapy based on the degree of posterior left bundle branch engagement.

21 Claims, 10 Drawing Sheets

(56) References Cited

U.S. PATENT DOCUMENTS

| | | |
|---|---|---|
| 4,250,884 A | 2/1981 | Hartlaub et al. |
| 4,256,115 A | 3/1981 | Bilitch |
| 4,263,919 A | 4/1981 | Levin |
| 4,280,502 A | 7/1981 | Baker, Jr. et al. |
| 4,289,144 A | 9/1981 | Gilman |
| 4,310,000 A | 1/1982 | Lindemans |
| 4,312,354 A | 1/1982 | Walters |
| 4,323,081 A | 4/1982 | Wiebusch |
| 4,332,259 A | 6/1982 | McCorkle, Jr. |
| 4,357,946 A | 11/1982 | Dutcher et al. |
| 4,365,639 A | 12/1982 | Goldreyer |
| 4,374,382 A | 2/1983 | Markowitz et al. |
| 4,393,883 A | 7/1983 | Smyth et al. |
| 4,440,173 A | 4/1984 | Hudziak et al. |
| 4,476,868 A | 10/1984 | Thompson |
| 4,479,500 A | 10/1984 | Smits |
| 4,522,208 A | 6/1985 | Buffet |
| 4,537,200 A | 8/1985 | Widrow |
| 4,546,777 A | 10/1985 | Groch et al. |
| 4,556,063 A | 12/1985 | Thompson et al. |
| 4,562,841 A | 1/1986 | Brockway et al. |
| 4,574,814 A | 3/1986 | Buffet |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,830,006 A | 5/1989 | Haluska et al. |
| 4,858,610 A | 8/1989 | Callaghan et al. |
| 4,865,037 A | 9/1989 | Chin et al. |
| 4,886,064 A | 12/1989 | Strandberg |
| 4,887,609 A | 12/1989 | Cole, Jr. |
| 4,928,688 A | 5/1990 | Mower |
| 4,953,564 A | 9/1990 | Berthelsen |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,107,850 A | 4/1992 | Olive |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grievous et al. |
| 5,133,353 A | 7/1992 | Hauser |
| 5,144,950 A | 9/1992 | Stoop et al. |
| 5,154,170 A | 10/1992 | Bennett et al. |
| 5,170,784 A | 12/1992 | Ramon |
| 5,174,289 A | 12/1992 | Cohen |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,255,692 A | 10/1993 | Neubauer et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,594 A | 6/1994 | Limousin et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yotntov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,554,177 A | 9/1996 | Kieval et al. |
| 5,562,711 A | 10/1996 | Yerich et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,140 A | 3/1998 | Salo et al. |
| 5,728,154 A | 3/1998 | Crossett et al. |
| 5,741,314 A | 4/1998 | Daly et al. |
| 5,741,315 A | 4/1998 | Lee et al. |
| 5,749,909 A | 5/1998 | Schroeppel et al. |
| 5,752,976 A | 5/1998 | Duffin et al. |
| 5,752,977 A | 5/1998 | Grievous et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,817,130 A | 10/1998 | Cox et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Cieiarelli et al. |
| 5,928,271 A | 7/1999 | Hess et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |

(56) References Cited

U.S. PATENT DOCUMENTS

| | | | |
|---|---|---|---|
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,132,456 A | 10/2000 | Sommer et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Cirevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,903 B1 | 9/2001 | Rosenthal et al. |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,508,771 B1 | 1/2003 | Padmanabhan et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,544,270 B1 | 4/2003 | Zhang |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,623,518 B2 | 9/2003 | Thompson et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,701,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,754,528 B2 | 6/2004 | Bardy et al. |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,869,404 B2 | 3/2005 | Schulhauser et al. |
| 6,871,095 B2 | 3/2005 | Stahmann et al. |
| 6,871,096 B2 | 3/2005 | Hill |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,931,286 B2 | 8/2005 | Sigg et al. |
| 6,934,585 B1 | 8/2005 | Schloss et al. |
| 6,941,169 B2 | 9/2005 | Pappu |
| 6,957,107 B2 | 10/2005 | Rogers et al. |
| 6,978,176 B2 | 12/2005 | Lattouf |
| 6,980,675 B2 | 12/2005 | Evron et al. |
| 6,985,773 B2 | 1/2006 | Von Arx et al. |
| 6,990,375 B2 | 1/2006 | Kloss et al. |
| 6,993,389 B2 | 1/2006 | Ding et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,176 B2 | 3/2006 | Ding et al. |
| 7,013,178 B2 | 3/2006 | Reinke et al. |
| 7,027,871 B2 | 4/2006 | Burnes et al. |
| 7,031,711 B2 | 4/2006 | Brown et al. |
| 7,031,771 B2 | 4/2006 | Brown et al. |
| 7,035,684 B2 | 4/2006 | Lee et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |

(56) References Cited

U.S. PATENT DOCUMENTS

| | | |
|---|---|---|
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,284 B2 | 2/2007 | Burnes et al. |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,231,248 B2 | 6/2007 | Kramer et al. |
| 7,231,253 B2 | 6/2007 | Tidemand et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,286,866 B2 | 10/2007 | Okerlund et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,307,321 B1 | 12/2007 | Avanzino |
| 7,308,297 B2 | 12/2007 | Reddy et al. |
| 7,308,299 B2 | 12/2007 | Burrell et al. |
| 7,310,556 B2 | 12/2007 | Bulkes |
| 7,317,950 B2 | 1/2008 | Lee |
| 7,319,905 B1 | 1/2008 | Morgan et al. |
| 7,321,677 B2 | 1/2008 | Evron et al. |
| 7,321,798 B2 | 1/2008 | Mlhienberg et al. |
| 7,333,853 B2 | 2/2008 | Mazar et al. |
| 7,336,994 B2 | 2/2008 | Hettrick et al. |
| 7,346,381 B2 | 3/2008 | Okerlund et al. |
| 7,346,393 B2 | 3/2008 | Spinelli et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,454,248 B2 | 11/2008 | Burrell et al. |
| 7,496,409 B2 | 2/2009 | Greenhut et al. |
| 7,496,410 B2 | 2/2009 | Heil |
| 7,499,743 B2 | 3/2009 | Vass et al. |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,546,166 B2 | 6/2009 | Michels et al. |
| 7,558,626 B2 | 7/2009 | Corbucci |
| 7,558,631 B2 | 7/2009 | Cowan et al. |
| 7,565,190 B2 | 7/2009 | Okerlund et al. |
| 7,565,195 B1 | 7/2009 | Kroll et al. |
| 7,584,002 B2 | 9/2009 | Burnes et al. |
| 7,587,074 B2 | 9/2009 | Zarkh et al. |
| 7,590,455 B2 | 9/2009 | Heruth et al. |
| 7,599,730 B2 | 10/2009 | Hunter et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,613,500 B2 | 11/2009 | Vass et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,764 B2 | 12/2009 | Ding et al. |
| 7,630,767 B1 | 12/2009 | Poore et al. |
| 7,634,313 B1 | 12/2009 | Kroll et al. |
| 7,635,541 B2 | 12/2009 | Scott et al. |
| 7,637,867 B2 | 12/2009 | Zdeblick |
| 7,640,057 B2 | 12/2009 | Libbus et al. |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,657,313 B2 | 2/2010 | Rom |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,706,879 B2 | 4/2010 | Burnes et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,629 B2 | 6/2010 | Zarkh et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,047 B2 | 6/2010 | Okerlund et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,778,685 B2 | 8/2010 | Evron et al. |
| 7,778,686 B2 | 8/2010 | Vass et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,813,785 B2 | 10/2010 | Okerlund et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |

(56) References Cited

U.S. PATENT DOCUMENTS

| | | |
|---|---|---|
| 7,877,142 B2 | 1/2011 | Moaddeb et al. |
| 7,877,144 B2 | 1/2011 | Coles, Jr. et al. |
| 7,881,786 B2 | 2/2011 | Jackson |
| 7,881,791 B2 | 2/2011 | Sambelashvili et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,891,915 B2 | 2/2011 | Chitre et al. |
| 7,894,885 B2 | 2/2011 | Bartal et al. |
| 7,894,894 B2 | 2/2011 | Stadler et al. |
| 7,894,902 B2 | 2/2011 | Rom |
| 7,894,907 B2 | 2/2011 | Cowan et al. |
| 7,894,910 B2 | 2/2011 | Cowan et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,912,544 B1 | 3/2011 | Min et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,027 B2 | 4/2011 | Prakash et al. |
| 7,930,040 B1 | 4/2011 | Kelsch et al. |
| 7,915,333 B2 | 5/2011 | Jacobson |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,941,218 B2 | 5/2011 | Sambelashvili et al. |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,063 B2 | 8/2011 | Vass et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,002,718 B2 | 8/2011 | Buchholtz et al. |
| 8,010,191 B2 | 8/2011 | Zhu et al. |
| 8,010,209 B2 | 8/2011 | Jacobson |
| 8,014,861 B2 | 9/2011 | Zhu et al. |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,065 B2 | 10/2011 | Burnes et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,185 B2 | 11/2011 | Hunter et al. |
| 8,060,212 B1 | 11/2011 | Rios et al. |
| 8,065,018 B2 | 11/2011 | Haubrich et al. |
| 8,068,920 B2 | 11/2011 | Gaudiani |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,105,714 B2 | 1/2012 | Schmidt et al. |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,145,308 B2 | 3/2012 | Sambelashvili et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,428 B2 | 5/2012 | Kaiser et al. |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,590 B2 | 6/2012 | Sambelashviii et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,041 B2 | 7/2012 | Van Gelder et al. |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,014 B2 | 11/2012 | Maskara et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,027 B2 | 1/2013 | Spinelli et al. |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,383,269 B2 | 2/2013 | Scott et al. |
| 8,386,051 B2 | 2/2013 | Rys |
| 8,391,964 B2 | 3/2013 | Musley et al. |
| 8,391,981 B2 | 3/2013 | Mosesov |
| 8,391,990 B2 | 3/2013 | Smith et al. |
| 8,401,616 B2 | 3/2013 | Verard et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,406,899 B2 | 3/2013 | Reddy et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,716 B2 | 4/2013 | Mullen et al. |
| 8,428,722 B2 | 4/2013 | Verhoef et al. |

(56) References Cited

U.S. PATENT DOCUMENTS

| | | |
|---|---|---|
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,467,871 B2 | 6/2013 | Maskara |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,509,916 B2 | 8/2013 | Byrd et al. |
| 8,515,559 B2 | 8/2013 | Roberts et al. |
| 8,521,268 B2 | 8/2013 | Zhang et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matoes |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,594,775 B2 | 11/2013 | Ghosh et al. |
| 8,612,002 B2 | 12/2013 | Faltys et al. |
| 8,615,310 B2 | 12/2013 | Khairkhahan et al. |
| 8,617,082 B2 | 12/2013 | Zhang et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,333 B2 | 1/2014 | Stadler et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,314 B2 | 3/2014 | Maskara et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | Dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,731,642 B2 | 5/2014 | Zarkh et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,750,994 B2 | 6/2014 | Ghosh et al. |
| 8,750,998 B1 | 6/2014 | Ghosh et al. |
| 8,755,884 B2 | 6/2014 | Demmer et al. |
| 8,758,365 B2 | 6/2014 | Bonner et al. |
| 8,768,459 B2 | 7/2014 | Ghosh et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,861,830 B2 | 10/2014 | Brada et al. |
| 8,868,186 B2 | 10/2014 | Kroll |
| 8,886,307 B2 | 11/2014 | Sambelashvili et al. |
| 8,886,311 B2 | 11/2014 | Anderson et al. |
| 8,886,339 B2 | 11/2014 | Faltys et al. |
| 8,903,473 B2 | 12/2014 | Rogers et al. |
| 8,903,513 B2 | 12/2014 | Ollivier |
| 8,909,336 B2 | 12/2014 | Navarro-Paredes et al. |
| 8,914,131 B2 | 12/2014 | Bornzin |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,948,883 B2 | 2/2015 | Eggen et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,033,996 B1 | 5/2015 | West |
| 9,037,262 B2 | 5/2015 | Regnier et al. |
| 9,042,984 B2 | 5/2015 | Demmer et al. |
| 9,072,872 B2 | 7/2015 | Asleson et al. |
| 9,072,911 B2 | 7/2015 | Hastings et al. |
| 9,072,913 B2 | 7/2015 | Jacobson |
| 9,101,281 B2 | 8/2015 | Reinert et al. |
| 9,119,959 B2 | 9/2015 | Rys et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,320,446 B2 | 4/2016 | Gillberg et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |

(56) References Cited

U.S. PATENT DOCUMENTS

| | | |
|---|---|---|
| 9,433,368 B2 | 9/2016 | Stahmann et al. |
| 9,433,780 B2 | 9/2016 | Regnier et al. |
| 9,457,193 B2 | 10/2016 | Klimovitch et al. |
| 9,474,457 B2 | 10/2016 | Ghosh et al. |
| 9,486,151 B2 | 11/2016 | Ghosh et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,517,336 B2 | 12/2016 | Eggen et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,579,500 B2 | 2/2017 | Rys et al. |
| 9,623,234 B2 | 4/2017 | Anderson |
| 9,636,511 B2 | 5/2017 | Carney et al. |
| 9,643,014 B2 | 5/2017 | Zhang et al. |
| 9,675,579 B2 | 6/2017 | Rock et al. |
| 9,707,399 B2 | 7/2017 | Zielinski et al. |
| 9,724,519 B2 | 8/2017 | Demmer et al. |
| 9,789,319 B2 | 10/2017 | Sambelashvili |
| 9,808,628 B2 | 11/2017 | Sheldon et al. |
| 9,808,633 B2 | 11/2017 | Bonner et al. |
| 9,877,789 B2 | 1/2018 | Ghosh |
| 9,924,884 B2 | 3/2018 | Ghosh et al. |
| 10,004,467 B2 | 6/2018 | Lahm et al. |
| 10,064,567 B2 | 9/2018 | Ghosh et al. |
| 10,099,050 B2 | 10/2018 | Chen et al. |
| 10,166,396 B2 | 1/2019 | Schrock et al. |
| 10,251,555 B2 | 4/2019 | Ghosh et al. |
| 10,406,370 B1 | 9/2019 | Makharinsky |
| 10,456,581 B2 | 10/2019 | Liu et al. |
| 10,478,627 B2 | 11/2019 | Muessig |
| 11,304,641 B2 * | 4/2022 | Ghosh .................. A61N 1/3956 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0004549 A1 | 1/2003 | Hill et al. |
| 2003/0009203 A1 | 1/2003 | Lebel et al. |
| 2003/0028082 A1 | 2/2003 | Thompson |
| 2003/0040779 A1 | 2/2003 | Engmarc et al. |
| 2003/0041866 A1 | 3/2003 | Linberg et al. |
| 2003/0045805 A1 | 3/2003 | Sheldon et al. |
| 2003/0083104 A1 | 5/2003 | Bonner et al. |
| 2003/0088278 A1 | 5/2003 | Bardy et al. |
| 2003/0092995 A1 | 5/2003 | Thompson |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0064158 A1 | 4/2004 | Klein et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 12/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0008210 A1 | 1/2005 | Evron et al. |
| 2005/0038477 A1 | 2/2005 | Kramer et al. |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0137629 A1 | 6/2005 | Dyjach et al. |
| 2005/0137671 A1 | 6/2005 | Liu et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0277990 A1 | 12/2005 | Ostroff et al. |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074285 A1 | 4/2006 | Zarkh et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0161205 A1 | 7/2006 | Mitrani et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0235478 A1 | 10/2006 | Van Gelder et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |

(56) References Cited

U.S. PATENT DOCUMENTS

| | | |
|---|---|---|
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0049975 A1 | 3/2007 | Cates et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0233216 A1 | 10/2007 | Liu et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299475 A1 | 12/2007 | Levin et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0103539 A1 | 5/2008 | Stegemann et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269816 A1 | 10/2008 | Prakash et al. |
| 2008/0269823 A1 | 10/2008 | Burnes et al. |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0234414 A1 | 3/2009 | Sambelashvili et al. |
| 2009/0088813 A1 | 4/2009 | Brockway et al. |
| 2009/0099619 A1 | 4/2009 | Lessmeier et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Jason |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0016914 A1 | 1/2010 | Mullen et al. |
| 2010/0023078 A1 | 1/2010 | Dong et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0063375 A1 | 3/2010 | Kassab et al. |
| 2010/0063562 A1 | 3/2010 | Cowan et al. |
| 2010/0065871 A1 | 3/2010 | Govari et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0152798 A1 | 6/2010 | Sanghera et al. |
| 2010/0168761 A1 | 7/2010 | Kassab et al. |
| 2010/0168819 A1 | 7/2010 | Freeberg |
| 2010/0185250 A1 | 7/2010 | Rom |
| 2010/0198288 A1 | 8/2010 | Ostroff |
| 2010/0198291 A1 | 8/2010 | Sambelashvili et al. |
| 2010/0198304 A1 | 8/2010 | Wang |
| 2010/0217367 A1 | 8/2010 | Belson |
| 2010/0218147 A1 | 8/2010 | Ishikawa |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286541 A1 | 11/2010 | Musley et al. |
| 2010/0286626 A1 | 11/2010 | Petersen |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Ideblick et al. |
| 2011/0071586 A1 | 3/2011 | Jacobson |
| 2011/0077708 A1 | 3/2011 | Ostroff |
| 2011/0098562 A1* | 4/2011 | Salgo .................. A61B 8/0883 600/437 |
| 2011/0106202 A1 | 5/2011 | Ding et al. |
| 2011/0112398 A1 | 5/2011 | Zarkh et al. |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway |
| 2011/0190841 A1 | 8/2011 | Sambelashvili et al. |
| 2011/0196444 A1 | 8/2011 | Prakash et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |

(56) References Cited

U.S. PATENT DOCUMENTS

| | | |
|---|---|---|
| 2012/0035685 A1 | 2/2012 | Saha et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0089214 A1 | 4/2012 | Kroll et al. |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109235 A1 | 5/2012 | Sheldon et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan |
| 2012/0215285 A1 | 8/2012 | Tahmasian et al. |
| 2012/0232478 A1 | 9/2012 | Haslinger |
| 2012/0232563 A1 | 9/2012 | Williams et al. |
| 2012/0232565 A1 | 9/2012 | Kveen et al. |
| 2012/0245665 A1 | 9/2012 | Friedman et al. |
| 2012/0263218 A1 | 10/2012 | Dal Molin et al. |
| 2012/0277600 A1 | 11/2012 | Greenhut |
| 2012/0277606 A1 | 11/2012 | Ellingson et al. |
| 2012/0277725 A1 | 11/2012 | Kassab et al. |
| 2012/0283587 A1 | 11/2012 | Gosh et al. |
| 2012/0283795 A1 | 11/2012 | Stancer et al. |
| 2012/0283807 A1 | 11/2012 | Deterre et al. |
| 2012/0284003 A1 | 11/2012 | Gosh et al. |
| 2012/0290025 A1 | 11/2012 | Keimel |
| 2012/0296228 A1 | 11/2012 | Zhang et al. |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0013017 A1 | 1/2013 | Mullen et al. |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053906 A1 | 2/2013 | Ghosh |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116739 A1 | 5/2013 | Brada et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0131750 A1 | 5/2013 | Stadler et al. |
| 2013/0131751 A1 | 5/2013 | Stadler et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197599 A1 | 8/2013 | Sambelashvili et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Walfhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268017 A1 | 10/2013 | Zhang et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0138006 A1 | 11/2013 | Bornzin et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0339570 A1 | 2/2014 | Carroll et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0114173 A1 | 4/2014 | Bar-Tal et al. |
| 2014/0114372 A1 | 4/2014 | Ghosh et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214164 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |

(56) References Cited

U.S. PATENT DOCUMENTS

| | | |
|---|---|---|
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0323882 A1 | 10/2014 | Ghosh et al. |
| 2014/0323892 A1 | 10/2014 | Ghosh et al. |
| 2014/0330208 A1 | 11/2014 | Christie et al. |
| 2014/0330287 A1 | 11/2014 | Thompson-Naumann et al. |
| 2014/0330326 A1 | 11/2014 | Thompson-Naumann et al. |
| 2014/0358135 A1 | 12/2014 | Sambelashvili et al. |
| 2014/0371832 A1 | 12/2014 | Ghosh |
| 2014/0371833 A1 | 12/2014 | Ghosh et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Foster et al. |
| 2015/0105836 A1 | 4/2015 | Bonner et al. |
| 2015/0142070 A1 | 5/2015 | Sambelashvili |
| 2015/0148697 A1 | 5/2015 | Burnes et al. |
| 2015/0149096 A1 | 5/2015 | Soykan |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0305695 A1 | 10/2015 | Lahm et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335894 A1 | 11/2015 | Bornzin et al. |
| 2016/0015287 A1 | 1/2016 | Anderson et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0045738 A1 | 2/2016 | Ghosh et al. |
| 2016/0045744 A1 | 2/2016 | Gillberg et al. |
| 2016/0051821 A1 | 2/2016 | Sambelashvili et al. |
| 2016/0059002 A1 | 3/2016 | Grubac et al. |
| 2016/0067486 A1 | 3/2016 | Brown et al. |
| 2016/0067487 A1 | 3/2016 | Demurer et al. |
| 2016/0067490 A1 | 3/2016 | Carney et al. |
| 2016/0110856 A1 | 4/2016 | Hoof et al. |
| 2016/0114161 A1 | 4/2016 | Amblard et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0129239 A1 | 5/2016 | Anderson |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0310733 A1 | 10/2016 | Sheldon et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056670 A1 | 3/2017 | Sheldon et al. |
| 2017/0182327 A1 | 6/2017 | Liu |
| 2017/0189681 A1 | 7/2017 | Anderson |
| 2017/0209689 A1 | 7/2017 | Chen |
| 2017/0216575 A1 | 8/2017 | Asleson et al. |
| 2017/0246461 A1* | 8/2017 | Ghosh .................. A61B 5/349 |
| 2017/0304624 A1 | 10/2017 | Friedman et al. |
| 2017/0326369 A1 | 11/2017 | Koop et al. |
| 2017/0340885 A1 | 11/2017 | Sambelashvili |
| 2018/0008829 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0050208 A1 | 2/2018 | Shuros et al. |
| 2018/0078773 A1 | 3/2018 | Thakur et al. |
| 2018/0078779 A1 | 3/2018 | An et al. |
| 2018/0117324 A1 | 5/2018 | Schilling et al. |
| 2018/0140848 A1 | 5/2018 | Stahmann |
| 2018/0178007 A1 | 6/2018 | Shuros et al. |
| 2018/0212451 A1 | 7/2018 | Schmidt et al. |
| 2018/0264262 A1 | 9/2018 | Haasl et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0280686 A1 | 10/2018 | Shuros et al. |
| 2018/0326215 A1 | 11/2018 | Ghosh |
| 2019/0030346 A1 | 1/2019 | Li |
| 2019/0038906 A1 | 2/2019 | Koop et al. |
| 2019/0083779 A1 | 3/2019 | Yang et al. |
| 2019/0083800 A1 | 3/2019 | Yang et al. |
| 2019/0083801 A1 | 3/2019 | Yang et al. |
| 2019/0192860 A1 | 6/2019 | Ghosh et al. |
| 2019/0269926 A1 | 9/2019 | Ghosh |
| 2019/0290909 A1 | 9/2019 | Ghosh |

FOREIGN PATENT DOCUMENTS

| | | |
|---|---|---|
| AU | 2014203793 A1 | 7/2014 |
| CN | 202933393 | 5/2013 |
| EP | 0362611 A1 | 4/1990 |
| EP | 0459 239 A2 | 12/1991 |
| EP | 0 728 497 A2 | 8/1996 |
| EP | 1 541 191 A1 | 6/2005 |
| EP | 1 702 648 A1 | 9/2006 |
| EP | 1 904 166 B1 | 6/2011 |
| EP | 2 452 721 A1 | 5/2012 |
| EP | 2 471 452 A1 | 7/2012 |
| EP | 2 662 113 A2 | 11/2013 |
| EP | 1 703 944 B1 | 7/2015 |
| JP | 2005245215 | 9/2005 |
| WO | WO 95/00202 | 1/1995 |
| WO | WO 96/36134 | 11/1996 |
| WO | WO 97/24981 | 7/1997 |
| WO | WO 02/22206 A1 | 3/2002 |
| WO | WO 03/092800 A1 | 11/2003 |
| WO | WO 2005/000206 A2 | 1/2005 |
| WO | WO 2005/042089 A1 | 5/2005 |
| WO | WO 2006/086435 A2 | 8/2006 |
| WO | WO 2006/113659 A1 | 10/2006 |
| WO | WO 2007/073435 A1 | 6/2007 |
| WO | WO 2007/075974 A2 | 7/2007 |
| WO | WO 2009/006531 A1 | 1/2009 |
| WO | WO 2013/080038 A2 | 6/2013 |
| WO | WO 2013/098644 A2 | 7/2013 |

(56) References Cited

FOREIGN PATENT DOCUMENTS

| | | |
|---|---|---|
| WO | WO 2015/081221 A1 | 6/2015 |
| WO | WO 2016/011042 A2 | 1/2016 |
| WO | WO 2016/077099 A1 | 5/2016 |
| WO | WO 2016/110856 A1 | 7/2016 |
| WO | WO 2016/171891 A1 | 10/2016 |
| WO | WO 2017/075193 A1 | 5/2017 |
| WO | WO 2018/009569 A1 | 1/2018 |
| WO | WO 2018/017226 A1 | 1/2018 |
| WO | WO 2018/017361 A1 | 1/2018 |
| WO | WO 2018/035343 A1 | 2/2018 |
| WO | WO 2018/081519 A1 | 5/2018 |

OTHER PUBLICATIONS http://www.isrctn.com/ISRCTN47824547, public posting published Aug. 2019.
Abed et al., "Obesity results in progressive atrial structural and electrical remodeling: Implications for atrial fibrillation," *Heart Rhythm Society*, Jan. 2013; 10(1):90-100.
Adragão et al., "Ablation of pulmonary vein foci for the treatment of atrial fibrillation; percutaneous electroanatomical guided approach," *Europace*, Oct. 2002; 4(4):391-9.
Aliot et al., "Arrhythmia detection by dual-chamber implantable cardioverter defibrillators: A review of current algorithms," *Europace*, Jul. 2004; 6(4):273-86.
Amirahmadi et al., "Ventricular Tachycardia Caused by Mesothelial Cyst," *Indian Pacing and Electrophysiology Journal*, 2013; 13(1):43-44.
Ammirabile et al., "Pitx2 confers left morphological, molecular, and functional identity to the sinus venosus myocardium," *Cardiovasc Res.*, Feb. 2012; 93(2):291-301.
Anderson et al., "Left bundle branch block and the evolving role of QRS morphology in selection of patients for cardiac resynchronization", Journal of Interventional Cardio Electrophysiology, vol. 52, No. 3. Aug. 20. 2018, pp. 353-374.
Anfinsen, "Non-pharmacological Treatment of Atrial Fibrillation," *Indian Pacing and Electrophysiology Journal*, Jan. 2002; 2(1):4-14.
Anné et al., "Ablation of post-surgical intra-atrial reentrant Tachycardia," *European Heart Journal*, 2002; 23:169-1616.
Arenal et al., "Dominant frequency differences in atrial fibrillation patients with and without left ventricular systolic dysfunction," *Europace*, Apr. 2009; 11(4):450-457.
Arriagada et al., "Predictors of arrhythmia recurrence in patients with lone atrial fibrillation," *Europace*, Jan. 2008; 10(1):9-14.
Asirvatham et al., "Cardiac Anatomic Considerations in Pediatric Electrophysiology," *Indian Pacing and Electrophysiology Journal*, Apr. 2008; 8(Suppl 1):S75-S91.
Asirvatham et al., "Intramyocardial Pacing and Sensing for the Enhancement of Cardiac Stimulation and Sensing Specificity," *Pacing Clin. Electrophysiol.*, Jun. 2007, 30(6):748-754.
Asirvatham et al., "Letter to the Editor," *J Cardiovasc Electrophysiol.*, Mar. 2010; 21(3): E77.
Balmer et al., "Long-term follow up of children with congenital complete atrioventricular block and the impact of pacemaker therapy," *Europace*, Oct. 2002; 4(4):345-349.
Barold et al., "Conventional and biventricular pacing in patients with first-degree atrioventricular block," *Europace*, Oct. 2012, 14(10):1414-9.
Barold et al., "The effect of hyperkalaemia on cardiac rhythm devices," *Europace*, Apr. 2014; 16(4):467-76.
Bayrak et al., "Added value of transoesophageal echocardiography during transseptal puncture performed by inexperienced operators," *Europace*, May 2012; 14(5):661-5.
Bergau et al., "Measurement of Left Atrial Pressure is a Good Predictor of Freedom From Atrial Fibrillation," *Indian Pacing and Electrophysiology Journal*, Jul. 2014; 14(4):181-93.
Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.
Bito et al., "Early exercise training after myocardial infarction prevents contractile but not electrical remodeling or hypertrophy," *Cardiovascular Research*, Apr. 2010; 86(1):72-81.
Bollmann et al., "Analysis of surface electrocardiograms in atrial fibrillation: techniques, research, and clinical applications," *Europace*, Nov. 2006; 8(11):911-926.
Bortone et al., "Evidence for an incomplete mitral isthmus block after failed ablation of a left postero-inferior concealed accessory pathway," *Europace*, Jun. 2006; 8(6):434-7.
Boulos et al., "Electroanatomical mapping and radiofrequency ablation of an accessory pathway associated with a large aneurysm of the coronary sinus," *Europace*, Nov. 2004, 6(6):608-12.
Brembilla-Perrot et al., "Incidence and prognostic significance of spontaneous and inducible antidromic tachycardia," *Europace*, Jun. 2013; 15(6):871-876.
Buber et al., "Morphological features of the P-waves at surface electrocardiogram as surrogate to mechanical function of the left atrium following a successful modified maze procedure," *Europace*, Apr. 2014; 16(4):578-86.
Burashnikov et al., "Late-phase 3 EAD. A unique mechanism contributing to initiation of atrial fibrillation," *Pacing Clin Electrophysiol.*, Mar. 2006; 29(3):290-5.
Burashnikov et al., "Atrial-selective inhibition of sodium-channel current by Wenxin Keli is effective in suppressing atrial fibrillation," *Heart Rhythm*, Jan. 2012, 9(1):125-31.
Calvo et al., "Efficacy of circumferential pulmonary vein ablation of atrial fibrillation in endurance athletes," *Europace*, Jan. 2010; 12(1):30-6.
Can et al., ""Atrial torsades de pointes" Induced by Low-Energy Shock From Implantable-Cardioverter Defibrillator," *Indian Pacing and Electrophysiology Journal*, Sep. 2013; 13(5):194-199.
Carroz et al., "Pseudo-pacemaker syndrome in a young woman with first-degree atrio-ventricular block," *Europace*, Apr. 2010; 12(4):594-596.
Catanchin et al., "Wolff-Parkinson-White syndrome with an unroofed coronary sinus without persistent left superior vena cava treated with catheter cryoablation," *Indian Pacing and Electrophysiology Journal*, Aug. 2008, 8(3):227-233.
Cazeau et al., "Cardiac resynchronization therapy," *Europace*, Sep. 2004; 5 Suppl 1:S42-8.
Cerqueira et al., "Standardized myocardial segmentation and nomenclature for tomographic imaging of the heart. A statement for healthcare professionals from the Cardiac Imaging Committee of the Council on Clinical Cardiology of the American Heart Association," *Circulation*, Jan. 29, 2002; 105(4):539-42.
Chandra et al., "Evaluation of KCB-328, a new IKr blocking antiarrhythmic agent in pacing induced canine atrial fibrillation," *Europace*, Sep. 2004; 6(5):384-91.
Chang et al., "Electrophysiological characteristics and catheter ablation in patients with paroxysmal supraventricular tachycardia and paroxysmal atrial fibrillation," *J Cardiovasc Electrophysiol.*, Apr. 2008; 19(4):367-73.
Charron et al., "A familial form of conduction defect related to a mutation in the PRKAG2 gene," *Europace*, Aug. 2007; 9(8):597-600.
Chou et al., "Effects of SEA0400 on Arrhythmogenicity in a Langendorff-Perfused 1-Month Myocardial Infarction Rabbit Model," *Pacing Clin Electrophysiol.*, May 2013; 36(5):596-606.
Ciploetta et al., "Posterior Coronary Vein as the Substrate for an Epicardial Accessory Pathway," *Indian Pacing and Electrophysiology Journal*, Aug. 2013; 13(4):142-7.
Climent et al., "Effects of endocardial microwave energy ablation," *Indian Pacing and Electrophysiology Journal*, Jul. 2005, 5(3):233-43.
Comtois et al., "Of circles and spirals: bridging the gap between the leading circle and spiral wave concepts of cardiac reentry," *Europace*, Sep. 2005; 7 Suppl 2:10-20.
Crick et al., "Anatomy of the pig heart: comparisons with normal human cardiac structure," *J. Anat.*,1998, 193:105-119.

(56) References Cited

OTHER PUBLICATIONS

Daoulah et al., "Unintended Harm and Benefit of the Implantable Defibrillator in an Unfortunate 19-Year-Old Male: Featuring a Sequence of Rare Life-threatening Complications of Cardiac Procedures," *Indian Pacing and Electrophysiology Journal*, Aug. 2013; 13(4):151-6.
De Mattia et al., "Paroxysmal atrial fibrillation triggered by a monomorphic ventricular couplet in a patient with acute coronary syndrome," *Indian Pacing and Electrophysiology Journal*, Jan. 2012; 12(1):19-23.
DeSimone et al., "New approach to cardiac resynchronization therapy: CRT without left ventricular lead," Apr. 25, 2014, 2 pages.
De Sisti et al., "Electrophysiological determinants of atrial fibrillation in sinus node dysfunction despite atrial pacing," *Europace*, Oct. 2000; 2(4):304-11.
De Voogt et al., "Electrical characteristics of low atrial septum pacing compared with right atrial appendage pacing," *Europace*, Jan. 2005; 7(1):60-6.
De Voogt et al., "A technique of lead insertion for low atrial septal pacing," *Pacing Clin Electrophysiol.*, Jul. 2005, 28(7):639-46.
Dizon et al. "Real-time stroke volume measurements for the optimization of cardiac resynchronization therapy parameters," *Europace*, Sep. 2010; 12(9):1270-1274.
Duckett et al., "Relationship between endocardial activation sequences defined by high-density mapping to early septal contraction (septal flash) in patients with left bundle branch block undergoing cardiac resynchronization therapy," *Europace*, Jan. 2012; 14(1):99-106.
Eksik et al., "Influence of atrioventricular nodal reentrant tachycardia ablation on right to left inter-atrial conduction," *Indian Pacing and Electrophysiology Journal*, Oct. 2005; 5(4):279-88.
Fiala et al., "Left Atrial Voltage during Atrial Fibrillation in Paroxysmal and Persistent Atrial Fibrillation Patients," *PACE*, May 2010; 33(5):541-548.
Fragakis et al., "Acute beta-adrenoceptor blockade improves efficacy of ibutilide in conversion of atrial fibrillation with a rapid ventricular rate," *Europace*, Jan. 2009; 11(1):70-4.
Frogoudaki et al., "Pacing for adult patients with left atrial isomerism: efficacy and technical considerations," *Europace*, Apr. 2003; 5(2):189-193.
Ganapathy et al., "Implantable Device to Monitor Cardiac Activity with Sternal Wires," *Pacing Clin. Electrophysiol.*, Dec. 2014; Epub Aug. 24, 2014; 37(12):1630-40.
Geddes, "Accuracy limitations of chronaxie values," *IEEE Trans Biomed Eng.*, Jan. 2004; 51(1):176-81.
Gertz et al., "The impact of mitral regurgitation on patients undergoing catheter ablation of atrial fibrillation," *Europace*, Aug. 2011; 13(8):1127-32.
Girmatsion et al., "Changes in microRNA-1 expression and IK1 up-regulation in human atrial fibrillation," *Heart Rhythm*, Dec. 2009; 6(12):1802-9.
Goette et al., "Acute atrial tachyarrhythmia induces angiotensin II type 1 receptor-mediated oxidative stress and microvascular flow abnormalities in the ventricles," *European Heart Journal*, Jun. 2009; 30(11):1411-20.
Goette et al., "Electrophysiological effects of angiotensin II. Part I: signal transduction and basic electrophysiological mechanisms," *Europace*, Feb. 2008; 10(2):238-41.
Gómez et al., "Nitric oxide inhibits Kv4.3 and human cardiac transient outward potassium current (Ito1)," *Cardiovasc Res.*, Dec. 2008; 80(3):375-84.
Gros et al., "Connexin 30 is expressed in the mouse sino-atrial node and modulates heart rate," *Cardiovascular Research*, Jan. 2010; 85(1):45-55.
Guenther et al., "Substernal Lead Implantation: A Novel Option to Manage OFT Failure in S-ICD patients," *Clinical Research Cardiology*, Feb. 2015, Epub Oct. 2, 2014; 104(2):189-91.
Guillem et al., "Noninvasive mapping of human atrial fibrillation," *J Cardiovasc Electrophysiol.*, May 2009; 20(5):507-513.

Hachisuka et al., "Development and Performance Analysis of an Intra-Body Communication Device," The 12th International Conference on Solid State Sensors, Actuators and Microsystems, vol. 4A1.3, pp. 1722-1725, 2003.
Hakacova et al., "Septal atrial pacing for the prevention of atrial fibrillation," *Europace*, 2007; 9:1124-1128.
Hasan et al., "Safety, efficacy, and performance of implanted recycled cardiac rhythm management (CRM) devices in underprivileged patients," *Pacing Clin Electrophysiol.*, Jun. 2011; 34(6):653-8.
Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.
He et al., "Three-dimensional cardiac electrical imaging from intracavity recordings," *IEEE Trans Biomed Eng.*, Aug. 2007; 54(8):1454-60.
Heist et al., "Direct visualization of epicardial structures and ablation utilizing a visually guided laser balloon catheter: preliminary findings," *J Cardiovasc Electrophysiol.*, Jul. 2011; 22(7):808-12.
Henz et al., "Synchronous Ventricular Pacing without Crossing the Tricuspid Valve or Entering the Coronary Sinus—Preliminary Results," *J Cardiovasc Electrophysiol.*, Dec. 2009; 20(12):1391-1397.
Hiippala et al., "Automatic Atrial Threshold Measurement and Adjustment in Pediatric Patients," *Pacing Clin Electrophysiol.*, Mar. 2010; 33(3):309-13.
Ho, "Letter to the Editor" *J Cardiovasc Electrophysiol.*, Mar. 2010; 21(3): E76.
Höijer et al., "Improved cardiac function and quality of life following upgrade to dual chamber pacing after long-term ventricular stimulation," *European Heart Journal*, Mar. 2002; 23(6):490-497.
Huang et al., "A Novel Pacing Strategy With Low and Stable Output: Pacing the Left Bundle Branch Immediately Beyond the Conduction Block," *Can J Cardiol.*, Dec. 2007; Epub Sep. 22, 2017; 33(12):1736.e1-1736.e.
Inter-Office Memo, Model 6426-85 Canine Feasibility AV Septal 8 mm Screw-In Right Single Pass DDD Lead Final Report (AR # 0120A0207).
Ishigaki et al., "Prevention of immediate recurrence of atrial fibrillation with low-dose landiolol after radiofrequency catheter ablation," *Journal of Arrhythmia*, Oct. 2015; 31(5):279-285.
Israel, "The role of pacing mode in the development of atrial fibrillation," *Europace*, Feb. 2006; 8(2):89-95.
Janion et al., "Dispersion of P wave duration and P wave vector in patients with atrial septal aneurysm," *Europace*, Jul. 2007; 9(7):471-4.
Kabra et al., "Recent Trends in Imaging for Atrial Fibrillation Ablation," *Indian Pacing and Electrophysiology Journal*, 2010; 10(5):215-227.
Kalbfleisch et al., "Catheter Ablation with Radiofrequency Energy: Biophysical Aspects and Clinical Applications," *Journal of Cardiovascular Electrophysiology*, Oct. 2008; 3(2):173-186.
Katritsis et al., "Classification and differential diagnosis of atrioventricular nodal re-entrant tachycardia," *Europace*, Jan. 2006; 8(1):29-36.
Katritsis et al., "Anatomically left-sided septal slow pathway ablation in dextrocardia and situs inversus totalis," *Europace*, Aug. 2008; 10(8):1004-5.
Khairy et al., "Cardiac Arrhythmias In Congenital Heart Diseases," *Indian Pacing and Electrophysiology Journal*, Nov.-Dec. 2009; 9(6):299-317.
Kimmel et al., "Single-site ventricular and biventricular pacing: investigation of latest depolarization strategy," *Europace*, Dec. 2007; 9(12):1163-1170.
Knackstedt et al., "Electro-anatomic mapping systems in arrhythmias," *Europace*, Nov. 2008; 10 Suppl 3:iii28-iii34.
Kobayashi et al., "Successful Ablation of Antero-septal Accessory Pathway in the Non-Coronary Cusp in a Child," *Indian Pacing and Electrophysiology Journal*, 2012; 12(3):124-130.
Kojodjojo et al., "4:2:1 conduction of an AF initiating trigger," *Indian Pacing and Electrophysiology Journal*, Nov. 2015, 15(5):255-8.

(56) References Cited

OTHER PUBLICATIONS

Kolodzińska et al., "Differences in encapsulating lead tissue in patients who underwent transvenous lead removal," *Europace*, Jul. 2012; 14(7):994-1001.
Konecny et al., "Synchronous intra-myocardial ventricular pacing without crossing the tricuspid valve or entering the coronary sinus," *Cardiovascular Revascularization Medicine*, 2013, 14:137-138.
Kriatselis et al., "Ectopic atrial tachycardias with early activation at His site: radiofrequency ablation through a retrograde approach," *Europace*, Jun. 2008; 10(6):698-704.
Lalu et al., "Ischaemia-reperfusion injury activates matrix metalloproteinases in the human heart," *Eur Heart J.*, Jan. 2005, 26(1):27-35.
Laske et al., "Excitation of the Intrinsic Conduction System Through His and Interventricular Septal Pacing," *Pacing Clin. Electrophysiol.*, Apr. 2006; 29(4):397-405.
Leclercq, "Problems and troubleshooting in regular follow-up of patients with cardiacdesynchronization therapy," *Europace*, Nov. 2009; 11 Suppl 5:v66-71.
Lee et al., "An unusual atrial tachycardia in a patient with Friedreich ataxia," *Europace*, Nov. 2011; 13(11):1660-1.
Lee et al., "Blunted Proarrhythmic Effect of Nicorandil in a Langendoiff-Perfused Phase-2 Myocardial Infarction Rabbit Model," *Pacing Clin Electrophysiol.*, Feb. 2013; 36(2):142-51.
Lemay et al., "Spatial dynamics of atrial activity assessed by the vectorcardiogram: from sinus rhythm to atrial fibrillation," *Europace*, Nov. 2007; 9 Suppl 6:vi109-18.
Levy et al., "Does the mechanism of action of biatrial pacing for atrial fibrillation involve changes in cardiac haemodynamics? Assessment by Doppler echocardiography and natriuretic peptide measurements," *Europace*, Apr. 2000; 2(2):127-35.
Lewalter et al., "Comparison of spontaneous atrial fibrillation electrogram potentials to the P wave electrogram amplitude in dual chamber pacing with unipolar atrial sensing," *Europace*, Apr. 2000; 2(2):136-40.
Liakopoulos et al., "Sequential deformation and physiological considerations in unipolar right and left ventricular pacing," *European Journal of Cardio-thoracic Surgery*, Apr. 1, 2006; 29S1:S188-197.
Lian et al., "Computer modeling of ventricular rhythm during atrial fibrillation and ventricular pacing," *IEEE Transactions on Biomedical Engineering*, Aug. 2006; 53(8):1512-1520.
Lim et al., "Right ventricular lead implantation facilitated by a guiding sheath in a patient with severe chamber dilatation with tricuspid regurgitation," *Indian Pacing and Electrophysiology Journal*, Sep. 2011; 11(5):156-8.
Lim et al., "Coupled pacing improves left ventricular function during simulated atrial fibrillation without mechanical dyssynchrony," *Europace*, Mar. 2010; 12(3):430-6.
Lou et al., "Tachy-brady arrhythmias: The critical role of adenosine-induced sinoatrial conduction block in post-tachycardia pauses," *Heart Rhythm.*, Jan. 2013; 10(1):110-8.
Lutomsky et al., "Catheter ablation of paroxysmal atrial fibrillation improves cardiac function: a prospective study on the impact of atrial fibrillation ablation on left ventricular function assessed by magnetic resonance imaging," *Europace*, May 2008; 10(5):593-9.
Macedo et al, "Septal accessory pathway: anatomy, causes for difficulty, and an approach to ablation," *Indian Pacing and Electrophysiology Journal*, Jul. 2010; 10(7):292-309.
Mafi-Rad et al., "Feasibility and Acute Hemodynamic Effect of Left Ventricular Septal Pacing by Transvenous Approach Through the Interventricular Septum," *Circ Arrhythm Electrophysoil.*, Mar. 2016; 9(3):e003344.
Mani et al., "Dual Atrioventricular Nodal Pathways Physiology: A Review of Relevant Anatomy, Electrophysiology, and Electrocardiographic Manifestations," *Indian Pacing and Electrophysiology Journal*, Jan. 2014; 14(1):12-25.
Manios et al., "Effects of successful cardioversion of persistent atrial fibrillation on right ventricular refractoriness and repolarization," *Europace*, Jan. 2005; 7(1):34-9.

Manolis et al., "Prevention of atrial fibrillation by inter-atrial septum pacing guided by electrophysiological testing, in patients with delayed interatrial conduction," *Europace*, Apr. 2002; 4(2):165-174.
Marino et al., "Inappropriate mode switching clarified by using a chest radiograph," *Journal of Arrhythmia*, Aug. 2015; 31(4):246-248.
Markowitz et al., "Time course and predictors of autonomic dysfunction after ablation of the slow atrioventricular nodal pathway," *Pacing Clin Electrophysiol.*, Dec. 2004; 27(12):1638-43.
Marshall et al., "The effects of temperature on cardiac pacing thresholds," *Pacing Clin Electrophysiol.*, Jul. 2010, 33(7):826-833.
McSharry et al., "A Dynamical Model for Generating Synthetic Electrocardiogram Signals," *IEEE Transactions on Biomedical Engineering*, Mar. 2003, 50(3):289-294.
Meijler et al., "Scaling of Atrioventricular Transmission in Mammalian Species: An Evolutionary Riddle!," *Journal of Cfardiovascular Electrophysiology*, Aug. 2002; 13(8):826-830.
Meiltz et al., "Permanent form of junctional reciprocating tachycardia in adults: peculiar features and results of radiofrequency catheter ablation," *Europace*, Jan. 2006; 8(1):21-8.
Mellin et al., "Transient reduction in myocardial free oxygen radical levels is involved in the improved cardiac function and structure after long-term allopurinol treatment initiated in established chronic heart failure," *Eur Heart J.*, Aug. 2005; 26(15):1544-50.
Mestan et al., "The influence of fluid and diuretic administration on the index of atrial contribution in sequentially paced patients," *Europace*, Apr. 2006; 8(4):273-8.
Metin et al., "Assessment of the P Wave Dispersion and Duration in Elite Women Basketball Players," *Indian Pacing and Electrophysiology Journal*, 2010, 10(1):11-20.
Mills et al., "Left Ventricular Septal and Left Ventricular Apical Pacing Chronically Maintain Cardiac Contractile Coordination, Pump Function and Efficiency," *Circ Arrhythm Electrophysoil.*, Oct. 2009, 2(5):571-579.
Mitchell et al., "How do atrial pacing algorithms prevent atrial arrhythmias?" *Europace*, Jul. 2004, 6(4):351-62.
Mirzoyev et al., "Embryology of the Conduction System for the Electrophysiologist," *Indian Pacing and Electrophysiology Journal*, 2010; 10(8):329-338.
Modre et al., "Noninvasive Myocardial Activation Time Imaging: A Novel Inverse Algorithm Applied to Clinical ECG Mapping Data," *IEE Transactions on Biomedical Engineering*, Oct. 2002; 49(10):1153-1161.
Montgomery et al., "Measurement of diffuse ventricular fibrosis with myocardial T1 in patients with atrial fibrillation," *J Arrhythm.*, Feb. 2016; 32(1):51-6.
Mulpuru et al., "Synchronous ventricular pacing with direct capture of the atrioventricular conduction system: Functional anatomy, terminology, and challenges," *Heart Rhythm*, Nov. 2016, Epub Aug. 3, 2016, 13(11):2237-2246.
Musa et al, "Inhibition of Platelet-Derived Growth Factor-AB Signaling Prevents Electromechanical Remodeling of Adult Atrial Myocytes that Contact Myofibroblasts," *Heart Rhythm*, Jul. 2013; 10(7):1044-1051.
Nagy et al., "Wnt-11 signalling controls ventricular myocardium development by patterning N-cadherin and β-catenin expression," *Cardiovascular Research*, Jan. 2010; 85(1):100-9.
Namboodiri et al., "Electrophysiological features of atrial flutter in cardiac sarcoidosis: a report of two cases," *Indian Pacing and Electrophysiology Journal*, Nov. 2012; 12(6):284-9.
Nanthakumar et al., "Assessment of accessory pathway and atrial refractoriness by transesophageal and intracardiac atrial stimulation: An analysis of methodological agreement," *Europace*, Jan. 1999; 1(1):55-62.
Neto et al., "Temporary atrial pacing in the prevention of postoperative atrial fibrillation," *Pacing Clin Electrophysiol.*, Jan. 2007; 30(Suppl 1):S79-83.
Nishijima et al., "Tetrahydrobiopterin depletion and NOS2 uncoupling contribute to heart failure-induced alterations in atrial electrophysiology," *Cardiovasc Res.*, Jul. 2011; 91(1):71-9.

(56) References Cited

OTHER PUBLICATIONS

Niwano et al., "Effect of oral L-type calcium channel blocker on repetitive paroxysmal atrial fibrillation: spectral analysis of fibrillation waves in the Holter monitoring," *Europace*, Dec. 2007, 9(12):1209-1215.

Okumura et al., "Effects of a high-fat diet on the electrical properties of porcine atria," *Journal of Arrhythmia*, Dec. 2015; 31(6):352-358.

Olesen et al., "Mutations in sodium channel β-subunit SCN3B are associated with early-onset lone atrial fibrillation," *Cardiovascular Research*, Mar. 2011; 89(4):786-93.

Ozmen et al., "P wave dispersion is increased in pulmonary stenosis," *Indian Pacing and Electrophysiology Journal*, Jan. 2006; 6(1):25-30.

Packer et al., "New generation of electro-anatomic mapping: Full intracardiac image integration," *Europace*, Nov. 2008, 10 Suppl 3:iii35-41.

Page et al., "Ischemic ventricular tachycardia presenting as a narrow complex tachycardia," *Indian Pacing and Electrophysiology Journal*, Jul. 2014; 14(4):203-210.

Pakarinen et al., "Pre-implant determinants of adequate long-term function of single lead VDD pacemakers," *Europace*, Apr. 2002; 4:137-141.

Patel et al., "Atrial Fibrillation after Cardiac Surgery: Where are we now?" *Indian Pacing and Electrophysiology Journal*, Oct.-Dec. 2008; 8(4):281-291.

Patel et al., "Successful ablation of a left-sided accessory pathway in a patient with coronary sinus atresia and arteriovenous fistula: clinical and developmental insights," *Indian Pacing and Electrophysiology Journal*, Mar. 2011; 11(2):43-49.

Peschar et al., "Left Ventricular Septal and Apex Pacing for Optimal Pump Function in Canine Hearts," *J Am Coll Cardiol.*, Apr. 2, 2003; 41(7):1218-1226.

Physiological Research Laboratories, Final Report for an Acute Study for Model 6426-85 AV Septal Leads, Feb. 1996.

Porciani et al., "Interatrial septum pacing avoids the adverse effect of interatrial delay in biventricular pacing: an echo-Doppler evaluation," *Europace*, Jul. 2002; 4(3):317-324.

Potse et al., "A Comparison of Monodomain and Bidomain Reaction-Diffusion Models for Action Potential Propagation in the Human Heart," *IEEE Transactions on Biomedical Engineering*, Dec. 2006; 53(12 Pt 1):2425-35.

Prystowsky et al., "Case studies with the experts: management decisions in atrial fibrillation," *J Cardiovasc Electrophysiol.*, Feb. 2008; 19(Suppl. 1):S1-12.

Prystowsky, "The history of atrial fibrillation: the last 100 years," *J Cardiovasc Electrophysiol*, Jun. 2008; 19(6):575-582.

Pytkowski et al., "Paroxysmal atrial fibrillation is associated with increased intra-atrial conduction delay," *Europace*, Dec. 2008; 10(12):1415-20.

Qu et al., "Dynamics and cardiac arrhythmias," *J Cardiovasc Electrophysiol.*, Sep. 2006; 17(9):1042-9.

Ravens et al., "Role of potassium currents in cardiac arrhythmias," *Europace*, Oct. 2008; 10(10):1133-7.

Ricci et al., "Efficacy of a dual chamber defibrillator with atrial antitachycardia functions in treating spontaneous atrial tachyarrhythmias in patients with life-threatening ventricular tachyarrhythmias, *European Heart Journal*, Sep. 2002; 23(18):1471-9.

Roberts-Thomson et al., "Focal atrial tachycardia II: management," *Pacing Clin Electrophysiol.*, Jul. 2006; 29(7):769-78.

Rossi et al., "Endocardial vagal atrioventricular node stimulation in humans: reproducibility on 18-month follow-up," *Europace*, Dec. 2010; 12(12):1719-24.

Rouzet et al., "Contraction delay of the RV outflow tract in patients with Brugada syndrome is dependent on the spontaneous ST-segment elevation pattern," *Heart Rhythm*, Dec. 2011; 8(12):1905-12.

Russo et al., "Atrial Fibrillation and Beta Thalassemia Major: The Predictive Role of the 12-lead Electrocardiogram Analysis," *Indian Pacing and Electrophysiology Journal*, May 2014; 14(3):121-32.

Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2): 219-22.

Sairaku et al., "Prediction of sinus node dysfunction in patients with persistent atrial flutter using the flutter cycle length," *Europace*, Mar. 2012, 14(3):380-7.

Santini et al., "Immediate and long-term atrial sensing stability in single-lead VDD pacing depends on right atrial dimensions," *Europace*, Oct. 2001; 3(4):324-31.

Saremi et al., "Cardiac Conduction System: Delineation of Anatomic Landmarks With Multi detector CT," *Indian Pacing and Electrophysiology Journal*, Nov. 2009; 9(6):318-33.

Savelieva et al., "Anti-arrhythmic drug therapy for atrial fibrillation: current anti-arrhythmic drugs, investigational agents, and innovative approaches," *Europace*, Jun. 2008; 10(6):647-665.

Schmidt et al., "Navigated DENSE strain imaging for post-radiofrequency ablation lesion assessment in the swine left atria," Europace, Jan. 2014; 16(1): 133-41.

Schoonderwoerd et al., "Rapid Pacing Results in Changes in Atrial but not in Ventricular Refractoriness," *Pacing Clin Electrophysiol.*, Mar. 2002; 25(3):287-90.

Schoonderwoerd et al., "Atrial natriuretic peptides during experimental atrial tachycardia: role of developing tachycardiomyopathy," *J Cardiovasc Electrophysiol.*, Aug. 2004; 15(8):927-32.

Schoonderwoerd et al., "Atrial ultrastructural changes during experimental atrial tachycardia depend on high ventricular rate," *J Cardiovasc Electrophysiol.*, Oct. 2004; 15(10):1167-74.

Sedmera, "Function and form in the developing cardiovascular system," *Cardiovasc Res.*, Jul. 2011; 91(2):252-9.

Severi et al., "Alterations of atrial electrophysiology induced by electrolyte variations: combined computational and P-wave analysis," *Europace*, Jun. 2010; 12(6):842-9.

Seyedi et al., "A Survey on Intrabody Communications for Body Area Network Application," IEEE Transactions on Biomedical Engineering, vol. 60(8): 2067-2079, 2013.

Shah et al., "Stable atrial sensing on long-term follow up of VDD pacemakers," *Indian Pacing and Electrophysiology Journal*, Oct. 2006; 6(4):189-93.

Shenthar et al., "Permanent pacemaker implantation in a patient with situs solitus, dextrocardia, and corrected transposition of the great arteries using a novel angiographic technique," *Journal of Arrhythmia*, Apr. 2014, 30(2):134-138.

Shenthar et al., "Transvenous permanent pacemaker implantation in dextrocardia: technique, challenges, outcome, and a brief review of literature," *Europace*, Sep. 2014; 16(9):1327-33.

Shirayama, "Role of atrial fibrillation threshold evaluation on guiding treatment," *Indian Pacing and Electrophysiology Journal*, Oct. 2003, 3(4):224-230.

Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.

Spickler et al., "Totally Self-Contained Intracardiac Pacemaker," Journal of Electrocardiology, vol. 3(3&4): 324-331, 1970.

Sreeram et al., "Indications for Electrophysiology Study in children," *Indian Pacing and Electrophysiology Journal*, Apr.-Jun. 2008; 8(Suppl. 1 ):S36-S54.

Stockburger et al., "Optimization of cardiac resynchronization guided by Doppler echocardiography: haemodynamic improvement and intraindividual variability with different pacing configurations and atrioventricular delays," *Europace*, Oct. 2006; 8(10):881-6.

Stroobandt et al., "Prediction of Wenckebach Behavior and Block Response in DDD Pacemakers," *Pacing Clin Electrophysiol.*, Jun. 2006, 9(6):1040-6.

Suenari et al., "Idiopathic left ventricular tachycardia with dual electrocardiogram morphologies in a single patient," *Europace*, Apr. 2010; 12(4):592-4.

Sweeney et al., "Analysis of Ventricular Activation Using Surface Electrocardiography to Predict Left Ventricular Reverse Volumetric Remodeling During Cardiac Resynchronization Therapy," Circulation, Feb. 9, 2010, 121(5): 626-34.

(56) References Cited

OTHER PUBLICATIONS

Tan et al., "Electrocardiographic evidence of ventricular repolarization remodelling during atrial fibrillation," *Europace*, Jan. 2008; 10(1):99-104.
Taramasco et al., "Internal low-energy cardioversion: a therapeutic option for restoring sinus rhythm in chronic atrial fibrillation after failure of external cardioversion," *Europace*, Jul. 1999; 1(3):179-82.
Testa et al., "Rate-control or rhythm-control: where do we stand?" *Indian Pacing and Electrophysiology Journal*, Oct. 2005; 5(4):296-304.
Thejus et al., "N-terminal Pro-Brain Natriuretic Peptide and Atrial Fibrillation," *Indian Pacing and Electrophysiology Journal*, Jan. 2009; 9(1):1-4.
Thornton et al., "Magnetic Assisted Navigation in Electrophysiology and Cardiac Resynchronisation: A Review," *Indian Pacing and Electrophysiology Journal*, Oct. 2006; 6(4):202-13.
Tilz et al., "In vivo left-ventricular contact force analysis: comparison of antegrade transseptal with retrograde transaortic mapping strategies and correlation of impedance and electrical amplitude with contact force," *Europace*, Sep. 2014; 16(9):1387-95.
Tomaske et al., "Do daily threshold trend fluctuations of epicardial leads correlate with pacing and sensing characteristics in paediatric patients?" *Europace*, Aug. 2007; 9(8):662-668.
Tomioka et al., "The effect of ventricular sequential contraction on helical heart during pacing: high septal pacing versus biventricular pacing," *European Journal of Cardio-thoracic Surgery*, Apr. 1, 2006; 29S1:S198-206.
Tournoux et al., "A 'Regularly Irregular' tachycardia: What is the diagnosis?" *Europace*, Dec. 2008; 10(12):1445-6.
Traykov et al., "Electrogram analysis at the His bundle region and the proximal coronary sinus as a tool to predict left atrial origin of focal atrial tachycardias," *Europace*, Jul. 2011; 13(7):1022-7.
Trudel et al., "Simulation of QRST integral maps with a membrane-based computer heart model employing parallel processing," *IEEE Trans Biomed Eng.*, Aug. 2004; 51(8):1319-29.
Tse et al., "Cardiac dynamics: Alternans and arrhythmogenesis," *Journal of Arrhythmia*, Oct. 2016; 32(5):411-417.
Tse, "Mechanisms of cardiac arrhythmias," *Journal of Arrhythmia*, Apr. 2016; 32(2):75-81.
Ueda et al., "Outcomes of single- or dual-chamber implantable cardioverter defibrillator systems in Japanese patients," *Journal of Arrhythmia*, Apr. 2016; 32(2):89-94.
Van Dam et al., "Volume conductor effects involved in the genesis of the P wave," *Europace*, Sep. 2005; 7 Suppl 2:30-8.
Van den Berg et al., "Depletion of atrial natriuretic peptide during longstanding atrial fibrillation," *Europace*, Sep. 2004; 6(5):433-7.
Van Deursen, et al., "Vectorcardiography as a Tool for Easy Optimization of Cardiac Resynchronization Therapy in Canine LBBB Hearts," *Circulation Arrhythmia and Electrophysiology*, Jun. 1, 2012, 5(3): 544-52.
Van Opstal et al., "Paradoxical increase of stimulus to atrium interval despite His-bundle capture during para-Hisian pacing," *Europace*, Dec. 2009; 11(12):1702-4.
Veenhuyzen et al., "Diagnostic pacing maneuvers for supraventricular tachycardia: part 1," *Pacing Clin Electrophysiol.*, Jun. 2011; 34(6):767-82.
Veenhuyzen et al., "Diagnostic pacing maneuvers for supraventricular tachycardias: part 2," *Pacing Clin Electrophysiol.*, Jun. 2012; 35(6):757-69.
Veenhuyzen et al., "Principles of Entrainment: Diagnostic Utility for Supraventricular Tachycardia," *Indian Pacing and Electrophysiology Journal*, 2008; 8(1):51-65.
Verbrugge et al., "Revisiting diastolic filling time as mechanistic insight for response to cardiac resynchronization therapy," *Europace*, Dec. 2013; 15(12):1747-56.
Verrier et al., "Mechanisms of ranolazine's dual protection against atrial and ventricular fibrillation," *Europace*, Mar. 2013; 15(3):317-324.

Verrijcken et al., "Pacemaker-mediated tachycardia with varying cycle length: what is the mechanism?" *Europace*, Oct. 2009; 11(10):1400-2.
Villani et al., "Reproducibility of internal atrial defibrillation threshold in paroxysmal and persistent atrial fibrillation," *Europace*, Jul. 2004; 6(4):267-72.
Vials et al., "Antioxidants for prevention of atrial fibrillation: a potentially useful future therapeutic approach? A review of the literature and meta-analysis," *Europace*, Aug. 2014; 16(8):1107-1116.
Weber et al., "Adenosine sensitive focal atrial tachycardia originating from the non-coronary aortic cusp," *Europace*, Jun. 2009; 11(6):823-6.
Weber et al., "Open-irrigated laser catheter ablation: relationship between the level of energy, myocardial thickness, and collateral damages in a dog model," *Europace*, Jan. 2014; 16(1):142-8.
Wegmoller, "Intra-Body Communication for Biomedical Sensor Networks," Diss. ETH, No. 17323, 1-173, 2007.
Wei et al., "Comparative simulation of excitation and body surface electrocardiogram with isotropic and anisotropic computer heart models," *IEEE Trans Biomed Eng.*, Apr. 1995; 42(4):343-57.
Weijs et al., "Clinical and echocardiographic correlates of intra-atrial conduction delay," *Europace*, Dec. 2011; 13(12):1681-7.
Weiss et al., "The influence of fibre orientation, extracted from different segments of the human left ventricle, on the activation and repolarization sequence: a simulation study," *Europace*, Nov. 2007; 9(Suppl, 6):vi96-vi104.
Wetzel et al., "A stepwise mapping approach for localization and ablation of ectopic right, left, and septal atrial foci using electroanatomic mapping," *European Heart Journal*, Sep. 2002; 23(17):1387-1393.
Wlodarska et al., "Thromboembolic complications in patients with arrhythmogenic right ventricular dysplasia/cardiomyopathy," *Europace*, Aug. 2006; 8(8):596-600.
Wong et al., "A review of mitral isthmus ablation," *Indian Pacing and Electrophysiology Journal*, 2012; 12(4):152-170.
Wu et al., "Acute and long-term outcome after catheter ablation of supraventricular tachycardia in patients after the Mustard or Senning operation for D-transposition of the great arteries," *Europace*, Jun. 2013; 15(6):886-91.
Xia et al., "Asymmetric dimethylarginine concentration and early recurrence of atrial fibrillation after electrical cardioversion," *Pacing Clin Electrophysiol.*, Aug. 2008; 31(8):1036-40.
Yamazaki et al., "Acute Regional Left Atrial Ischemia Causes Acceleration of Atrial Drivers during Atrial Fibrillation," *Heart Rhythm*, Jun. 2013; 10(6):901-9.
Yang et al., "Focal atrial tachycardia originating from the distal portion of the left atrial appendage: Characteristics and long-term outcomes of radiofrequency ablation," *Europace*, Feb. 2012; 14(2):254-60.
Yiginer et al., "Advanced Age, Female Gender and. Delay in Pacemaker Implantation May Cause TdP in Patients With Complete Atrioventricular Block," *Indian Pacing and Electrophysiology Journal*, Oct. 2010; 10(10):454-63.
Yoon et al., "Measurement of thoracic current flow in pigs for the study of defibrillation and cardioversion," *IEEE Transactions on Biomedical Engineering*, Oct. 2003; 50(10):1167-1773.
Yuan et al., "Recording monophasic action potentials using a platinum-electrode ablation catheter," *Europace*, Oct. 2000; 2(4):312-9.
Yusuf et al., "5-Hydroxytryptamine and Atrial Fibrillation: How Significant is This Piece in the Puzzle?" *J Cardiovasc Electrophysiol.*, Feb. 2003; 14(2):209-14.
Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2):85-92.
Zhang et al., "Acuteatrial arrhythmogenicity and altered Ca(2+) homeostasis in murine RyR2-P2328S hearts," *Cardiovascular Research*, Mar. 2011; 89(4):794-804.
Zoghi et al., "Electrical stunning and hibernation: suggestion of new terms for short-and long-term cardiac memory," *Europace*, Sep. 2004; 6(5):418-24.

(56) References Cited

OTHER PUBLICATIONS

Zografos et al., "Inhibition of the renin-angiotensin system for prevention of atrial fibrillation," *Pacing Clin Electrophysiol.*, Oct. 2010; 33(10):1270-85.

(PCT/US2014/066792) PCT Notification of Transmittal of the International Search Report and the Written Opinion of the International Searching Authority.

(PCT/US2014/013601) PCT Notification of Transmittal of the International Search Report and the Written Opinion of the International Searching Authority.

(PCT/US2014/036782) PCT Notification of Transmittal of the International Search Report and the Written Opinion of the International Searching Authority, dated Aug. 22, 2014, 11 pages.

International Search Report and Written Opinion for Application No. PCT/US2017/047378, 8 pages, dated Dec. 6, 2017.

(PCT/US2018/050988) PCT Notification of Transmittal of the International Search Report and the Written Opinion of the International Searching Authority, dated Nov. 14, 2018, 11 pages.

(PCT/US2018/050993) PCT Notification of Transmittal of the International Search Report and the Written Opinion of the International Searching Authority, dated Nov. 16, 2018, 7 pages.

(PCT/US2019/023642) PCT Notification of Transmittal of the International Search Report and the Written Opinion of the international Searching Authority, dated Jun. 28, 2019, 14 pages.

(PCT/US2019/023645) PCT Notification of Transmittal of the International Search Report and the Written Opinion of the International Searching Authority, dated Sep. 4, 2019, 14 pages.

(PCT/US2019/023646) PCT Notification of Transmittal of the International Search Report and the Written Opinion of the International Searching Authority, dated Aug. 19, 2019, 15 pages.

(PCT/IB2019/057352) PCT Notification of Transmittal of the International Search Report and the Written Opinion of the International Searching Authority, dated Nov. 27, 2019, 123 pages.

International Search Report and Written Opinion for Application No. PCT/US2020/023525, 10 pages, dated Jul. 9, 2020.

\* cited by examiner

MPAT: 21ms

MPAT: 44ms

MPAT: 80ms

POSTERIOR LEFT BUNDLE BRANCH ENGAGEMENT

The disclosure herein relates to systems and methods for use in determining posterior left bundle branch engagement by cardiac therapy.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on or in the heart. In some cases, the equipment provides information to the physician about the electrical activity of the heart and the location of the intracardiac lead.

SUMMARY

The illustrative systems and methods described herein may be configured to assist a user (e.g., a physician) in evaluating a patient's posterior left bundle branch engagement (e.g., whether or not the patient's posterior left bundle branch is engaged) by cardiac therapy (e.g., cardiac conduction system pacing therapy, traditional, non-conduction system pacing therapy, etc.). More specifically, for example, the illustrative systems and methods may be used to determine the degree of posterior left bundle branch engagement based on monitored electrical activity. The monitored electrical activity may be used to generate, or compute, electrical heterogeneity information that is directed towards posterior left bundle branch engagement. Further, the illustrative systems and methods described herein may be configured to assist a user (e.g., a physician) in adjusting cardiac therapy based on evaluation of engagement of the patient's posterior left bundle branch by the cardiac therapy.

In one or more embodiments, the systems and methods may be described as being noninvasive. For example, in some embodiments, the systems and methods may not need, or include, implantable devices such as leads, probes, sensors, catheters, implantable electrodes, etc. to monitor, or acquire, electrical activity (e.g., a plurality of cardiac signals) from tissue of the patient for use in evaluating engagement of the patient's posterior left bundle branch by cardiac therapy. Instead, the systems and methods may use electrical measurements taken noninvasively using, e.g., a plurality of external electrodes attached to the skin of a patient about the patient's torso. In one or more embodiments, the systems and methods may be described as being invasive in that such systems and methods may utilize implantable electrodes to monitor electrical activity for using in evaluating engagement of the patient's posterior left bundle branch by cardiac therapy. Additionally, it is be understood that both invasive and non-invasive apparatus and processes may be used at the same time or simultaneously in some embodiments.

It may be described that the present disclosure provides qualitative and quantitative feedback on engagement of the posterior left bundle when delivering cardiac therapy such as, e.g., VfA pacing therapy. One of the objectives of VfA pacing therapy may be to engage the posterior left bundle for rapid propagation of electrical activation. Illustrative systems and methods described herein may include electrode apparatus (e.g., "ECG belt") that may be used as a surface mapping tool that helps visualize electrical activation on "body surface" activation maps.

The present disclosure provides various metrics disclosed that would be reflective of the degree of engagement of posterior fascicle during cardiac therapy such as, e.g., VfA pacing, left bundle branch (LBB) pacing, etc. Accordingly pacing electrode position, pacing thresholds of complete engagement of posterior fascicle, and other pacing parameters (e.g., pacing vectors, pacing amplitude, pacing pulse length, timing delays such as A-V delay and V-V delay, etc.) may be adjusted to get, or provide, "complete" or maximum engagement of left posterior bundle from cardiac pacing therapy pacing (e.g., VfA pacing with a leadless or leaded device). These pacing thresholds and parameters may be different from the pacing thresholds and parameters using for traditional myocardial tissue capture.

The present disclosure describes systems and methods that provide more efficient resynchronization (e.g., using VfA pacing, LBB pacing, left ventricular septal basal pacing, etc.) based on engagement of posterior fascicle or posterior LBB, which if done successfully should result in complete preactivation of posterior surface of the body as reflected on the surrogate activation time maps. Further, the new metrics disclosed herein may also be used and tied to the concept of titration of pacing to maximize engagement of left posterior bundle.

An illustrative metric of electrical heterogeneity information (EHI) may be an average activation time of posterior electrodes (e.g., a subset of electrodes placed in proximity with the posterior of the patient such as the posterior torso of the patient), which may be referred to as the mean posterior activation time (MPAT). Another illustrative metric of EHI may be the percentage of posterior electrodes activating earlier than a certain time threshold (e.g., 35 milliseconds), which may be referred to as a percentage of early posterior activation (PEPA), indicating a degree of spread of early activation on the posterior aspect of the body.

Such illustrative metrics of EHI may be used to reflect the degree of engagement of posterior bundle during cardiac therapy such as, e.g., VfA pacing. For example, a MPAT that is less than or equal to 30 milliseconds (ms) and a PEPA that is greater than or equal to 75% may be reflective of complete posterior bundle engagement. Further, a MPAT that is between 30 ms and 50 ms and a PEP that is between 50% and 75% may be reflective of intermediate posterior bundle engagement. Still further, any other values of MPAT and PEPA may be reflective of insufficient posterior bundle engagement.

The illustrative systems and methods may utilize the illustrative metrics of EHI to adjust one or more cardiac therapy parameters (e.g., pacing parameters such as pacing output, pacing vector, site of pacing, etc.). Thus, one or more cardiac therapy parameters may be "tuned" with a goal towards complete posterior bundle engagement indicated by a lower value of MPAT and a higher value of PEPA. Further, cardiac therapy parameters may be set to maximize the extent of engagement of posterior left bundle. An illustrative cardiac therapy system or device may store such cardiac therapy parameters in memory and accordingly set safety margins above basic tissue capture thresholds for the cardiac therapy delivered thereby.

Further, the illustrative systems and methods may qualitatively indicate the degree of engagement may in terms of colors on the posterior maps coded with shades of red for early and green/blue for late activation. Complete red on posterior map of the belt may imply complete engagement. Lesser extent of red on posterior map corresponds to lesser extent of engagement of posterior bundle.

Successful resynchronization using, e.g., VfA pacing, may be partly dependent on degree of engagement of posterior left bundle that results in rapid propagation of activation in posterior/posterolateral part of left ventricle. The illustrative systems and methods described herein provide ways to assess the degree of engagement of posterior left bundle non-invasively with electrode apparatus, which may assist in providing effective cardiac therapy.

One illustrative system may include electrode apparatus comprising a plurality of posterior electrodes to monitor electrical activity from a patient's posterior and computing apparatus comprising processing circuitry and coupled to the electrode apparatus. The computing apparatus may be configured to monitor electrical activity of the patient's heart using the plurality of posterior electrodes during delivery of cardiac therapy, generate electrical heterogeneity information (EHI) based on the monitored electrical activity during delivery of cardiac therapy, and determine a degree of posterior left bundle branch engagement based on the generated EHI.

One illustrative method may include monitoring electrical activity of the patient's heart using a plurality of posterior electrodes from a patient's posterior during delivery of cardiac therapy, generating electrical heterogeneity information (EHI) based on the monitored electrical activity during delivery of cardiac therapy, and determining a degree of posterior left bundle branch engagement based on the generated EHI.

One illustrative system may include electrode apparatus comprising a plurality of posterior electrodes to monitor electrical activity from a patient's posterior and computing apparatus comprising processing circuitry and coupled to the electrode apparatus. The computing apparatus configured to monitor electrical activity of the patient's heart using the plurality of posterior electrodes during delivery of cardiac pacing therapy, determine a degree of posterior left bundle branch engagement based on the monitored electrical activity, and adjust one or more pacing settings of the cardiac pacing therapy based on the determined degree of left bunch branch engagement.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF ILLUSTRATIVE EMBODIMENTS

Figure 1:
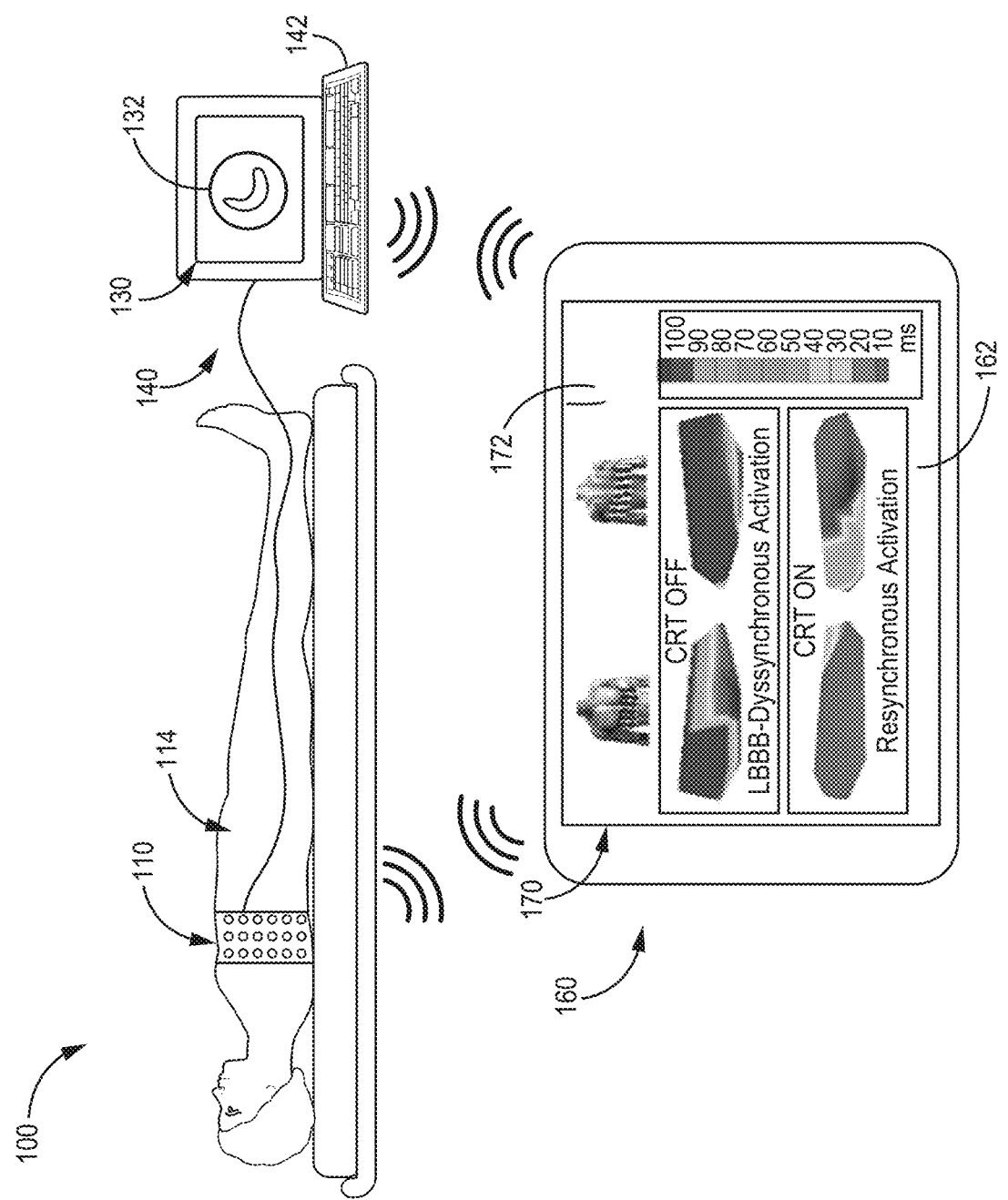
FIG. 1 is a diagram of an illustrative system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Illustrative systems and methods shall be described with reference to FIGS. 1-10. It will be apparent to one skilled in the art that elements or processes from one embodiment may be used in combination with elements or processes of the other embodiments, and that the possible embodiments of such systems, methods, and devices using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Various illustrative systems, methods, and graphical user interfaces may be configured to use electrode apparatus including external electrodes, display apparatus, and computing apparatus to noninvasively assist a user (e.g., a physician) in the evaluation of posterior left bundle branch engagement by cardiac therapy and/or the configuration (e.g., optimization) of the cardiac therapy based on the evaluation. An illustrative system 100 including electrode apparatus 110, computing apparatus 140, and a remote computing device 160 is depicted in FIG. 1.

The electrode apparatus 110 as shown includes a plurality of electrodes incorporated, or included, within a band wrapped around the chest, or torso, of a patient 114. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, illustrative electrode apparatus 110 will be described in more detail in reference to FIGS. 2-3.

The computing apparatus 140 and the remote computing device 160 may each include display apparatus 130, 170, respectively, that may be configured to display data such as, e.g., electrical signals (e.g., electrocardiogram data), electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the assessment and evaluation of posterior left bundle branch engagement. More specifically, for example, the QRS complex of a single cardiac cycle may be evaluated for one or more metrics such as, e.g., QRS onset, QRS offset, QRS peak, various electrical heterogeneity information (EHI) such as electrical activation times, left ventricular or thoracic standard deviation of electrical activation times (LVED), standard deviation of activation times (SDAT), average left ventricular or thoracic surrogate electrical activation times (LVAT), and referenced to earliest activation time, QRS duration (e.g., interval between QRS onset to QRS offset), difference between average left surrogate and average right surrogate activation times, relative or absolute QRS morphology, differences between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, one or both of the computing apparatus 140 and the remote computing device 160 may be a server, a personal computer, or a tablet computer. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining EHI, for determining QRS onsets, QRS offsets, medians, modes, averages, peaks or maximum values, valleys or minimum values, for determining electrical activation times, for evaluating posterior left bundle branch engagement by cardiac therapy, for determining whether the patient has left or right ventricular delays or blocks, for determining whether one or more adjustments to pacing settings of cardiac therapy may increase posterior left bundle branch engagement, for driving a graphical user interface configured to noninvasively assist a user in configuring one or more pacing parameters, or settings, such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., biventricular pacing, right ventricle only pacing, left ventricle only pacing, etc.), and arrhythmia detection and treatment, rate adaptive settings and performance, etc.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to view and/or select one or more pieces of cardiac therapy configuration information, posterior left bundle branch engagement information (e.g., degree of posterior left bundle branch engagement, indication of whether posterior left bundle branch engagement is sufficiently, partially, or insufficiently been engaged, by cardiac therapy, etc.), and electrical heterogeneity information.

Although as depicted the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of electrical activation, a plurality of signals for the external electrodes over one or more heartbeats, QRS complexes, various cardiac therapy scenario selection regions, various rankings of cardiac therapy scenarios, various pacing parameters, electrical heterogeneity information (EHI), textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

It is to be understood that the computing apparatus 140 and the remote computing device 160 may be operatively coupled to each other in a plurality of different ways so as to perform, or execute, the functionality described herein. For example, in the embodiment depicted, the computing device 140 may be wireless operably coupled to the remote computing device 160 as depicted by the wireless signal lines emanating therebetween. Additionally, as opposed to wireless connections, one or more of the computing apparatus 140 and the remoting computing device 160 may be operably coupled through one or wired electrical connections.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more illustrative methods and/or processes described herein. Data stored and/or used by the computing apparatus 140 and the remote computing device 160 may include, for example, electrical signal/waveform data from the electrode apparatus 110 (e.g., a plurality of QRS complexes), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for executing, or performing, the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform the functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and interfaces may be implemented using a computer readable storage medium, configured with a computer program, where the storage medium so configured causes the computer to operate in a specific and predefined manner to perform functions described herein. Further, in at least one embodiment, the illustrative systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
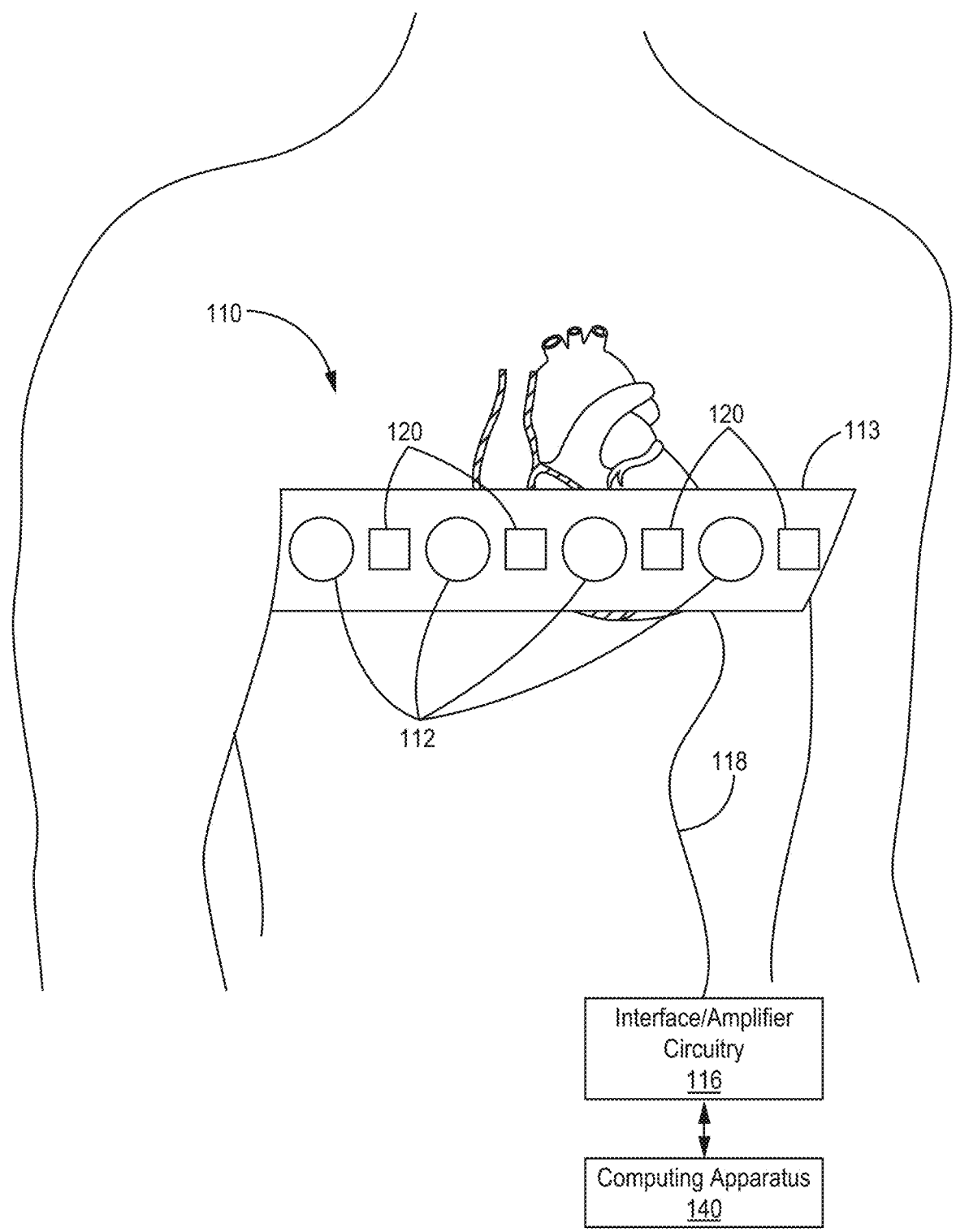
FIGS. 2-3 are diagrams of illustrative external electrode apparatus for measuring torso-surface potentials.

The illustrative electrode apparatus 110 may be configured to measure body-surface potentials of a patient 114 and, more particularly, torso-surface potentials of a patient 114. As shown in FIG. 2, the illustrative electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 114 such that the electrodes 112 surround the patient's heart. As further illustrated, the electrodes 112 may be positioned around the circumference of a patient 114, including the posterior, lateral, posterolateral, anterolateral, and anterior locations of the torso of a patient 114.

The illustrative electrode apparatus 110 may be further configured to measure, or monitor, sounds from the patient 114 (e.g., heart sounds from the torso of the patient). As shown in FIG. 2, the illustrative electrode apparatus 110 may include a set, or array, of acoustic sensors 120 attached, or coupled, to the strap 113. The strap 113 may be configured to be wrapped around the torso of a patient 114 such that the acoustic sensors 120 surround the patient's heart. As further illustrated, the acoustic sensors 120 may be positioned around the circumference of a patient 114, including the posterior, lateral, posterolateral, anterolateral, and anterior locations of the torso of a patient 114.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other illustrative systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to one or both of the computing apparatus 140 and the remote computing device 160 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 114. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 114. Still further, in other examples, one or both of the electrodes 112 and the acoustic sensors 120 may be part of, or located within, two sections of material or two patches. One of the two patches may be located on the anterior side of the torso of the patient 114 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 114 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 114 across the left side of the patient 114 to the posterior side of the patient 114. Yet still further, in other examples, one or both of the electrodes 112 and the acoustic sensors 120 may be arranged in a curve around the armpit area and may have an electrode/sensor-density that is less dense on the right thorax that the other remaining areas.

The electrodes 112 may be configured to surround the heart of the patient 114 and record, or monitor, the electrical signals associated with the depolarization and repolarization of the heart after the signals have propagated through the torso of a patient 114. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, there may be about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 114. Instead, the electrodes 112 and acoustic sensors 120 may be arranged in an array that extends only part of the way or partially around the patient 114. For example, the electrodes 112 and acoustic sensors 120 may be distributed on the anterior, posterior, and left sides of the patient with less or no electrodes and acoustic sensors proximate the right side (including posterior and anterior regions of the right side of the patient).

One or both of the computing apparatus 140 and the remote computing device 160 may record and analyze the torso-surface potential signals sensed by electrodes 112 and the sound signals sensed by the acoustic sensors 120, which are amplified/conditioned by the interface/amplifier circuitry 116. Further, one or both of the computing apparatus 140 and the remote computing device 160 may be configured to analyze the electrical signals from the electrodes 112 to provide electrocardiogram (ECG) signals, information such as EHI, or data from the patient's heart as will be further described herein. Still further, one or both of the computing apparatus 140 and the remote computing device 160 may be configured to analyze the electrical signals from the acoustic sensors 120 to provide sound signals, information, or data from the patient's body and/or devices implanted therein (such as a left ventricular assist device).

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict electrical activation maps and EHI obtained using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Illustrative systems and methods may noninvasively use the electrical information collected using the electrode apparatus 110 and the sound information collected using the acoustic sensors 120 to evaluate a patient's cardiac health and to evaluate and configure cardiac therapy being delivered to the patient. More specifically, the illustrative systems and methods may noninvasively use the electrical information collected using the electrode apparatus 110 to determine whether the patient's posterior left bundle branch has been engaged by cardiac therapy, and for example, to what degree the patient's posterior left bundle branch has been engaged.

Further, the electrode apparatus 110 may further include reference electrodes and/or drive electrodes to be, e.g. positioned about the lower torso of the patient 114, that may be further used by the system 100. For example, the electrode apparatus 110 may include three reference electrodes, and the signals from the three reference electrodes may be combined to provide a reference signal. Further, the electrode apparatus 110 may use three caudal reference electrodes (e.g., instead of standard reference electrodes used in a Wilson Central Terminal) to get a "true" unipolar signal with less noise from averaging three caudally located reference signals.

Figure 3:
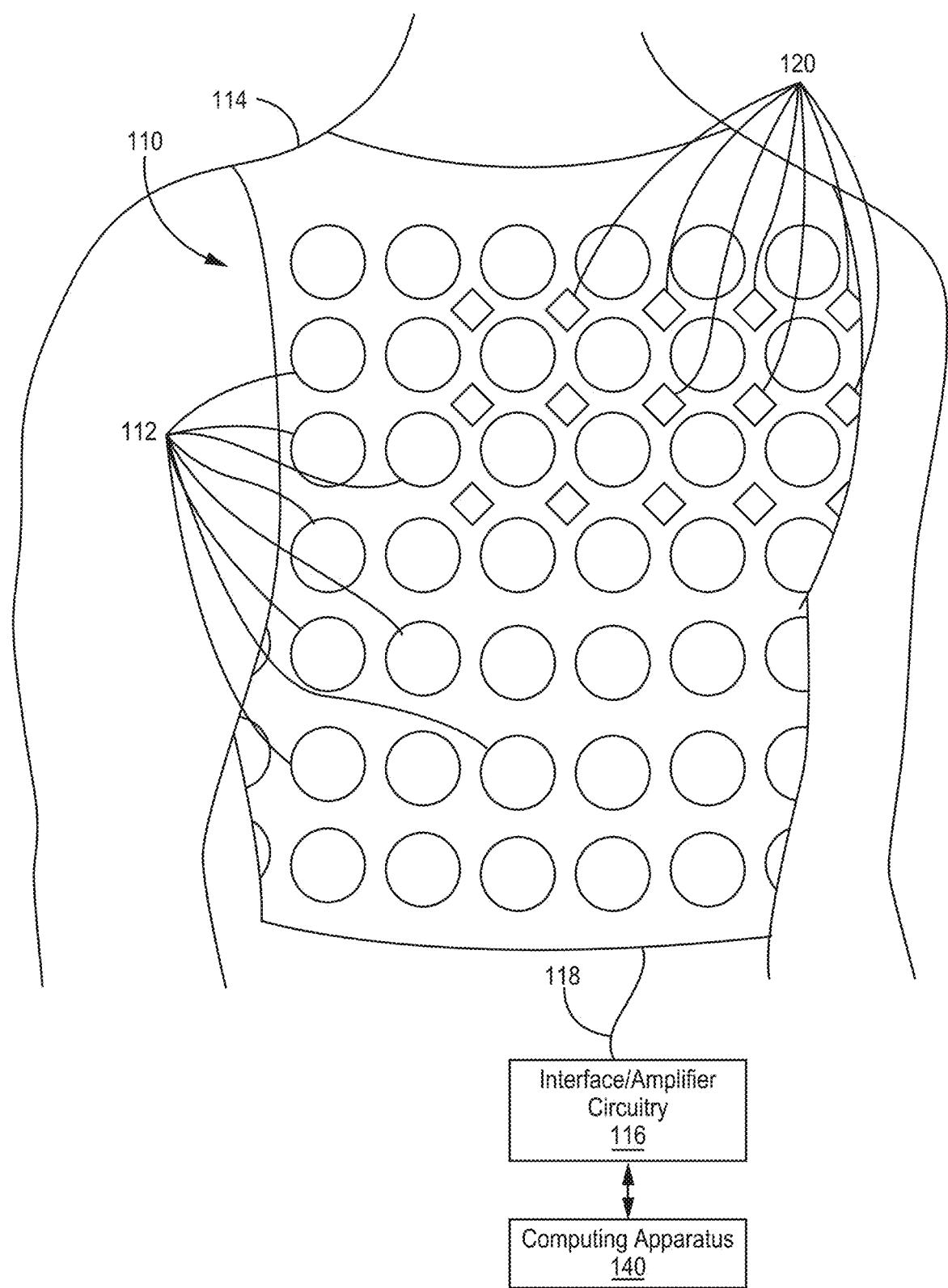

FIG. 3 illustrates another illustrative electrode apparatus 110 that includes a plurality of electrodes 112 configured to surround the heart of the patient 114 and record, or monitor, the electrical signals associated with the depolarization and repolarization of the heart after the signals have propagated through the torso of the patient 114 and a plurality of acoustic sensors 120 configured to surround the heart of the patient 114 and record, or monitor, the sound signals associated with the heart after the signals have propagated through the torso of the patient 114. The electrode apparatus 110 may include a vest 114 upon which the plurality of electrodes 112 and the plurality of acoustic sensors 120 may be attached, or to which the electrodes 112 and the acoustic sensors 120 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 114, including, for example, the posterior, lateral, posterolateral, anterolateral, and anterior locations of the torso of a patient 114.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 114. Further, the vest 114 may be marked to assist in determining the location of the electrodes 112 and the acoustic sensors 120 on the surface of the torso of the patient 114. In some examples, there may be about 25 to about 256 electrodes 112 and about 25 to about 256 acoustic sensors 120 distributed around the torso of the patient 114, though other configurations may have more or fewer electrodes 112 and more or fewer acoustic sensors 120.

The illustrative systems and methods described herein may be used to provide noninvasive assistance to a user in the evaluation and assessment of posterior left bundle branch engagement by cardiac therapy such as VfA cardiac pacing, left ventricular septal-basal cardiac pacing, etc. Further, the illustrative systems and methods described herein may be used in the configuration of cardiac therapy being presently-delivered to the patient (e.g., by an implantable medical device such as a VfA pacing device). For example, the illustrative systems and methods may be used to assist a user in the improvement of posterior left bundle branch activation by providing guidance to a user in adjusting cardiac therapy and/or automatically adjusting the cardiac therapy.

Figure 4:
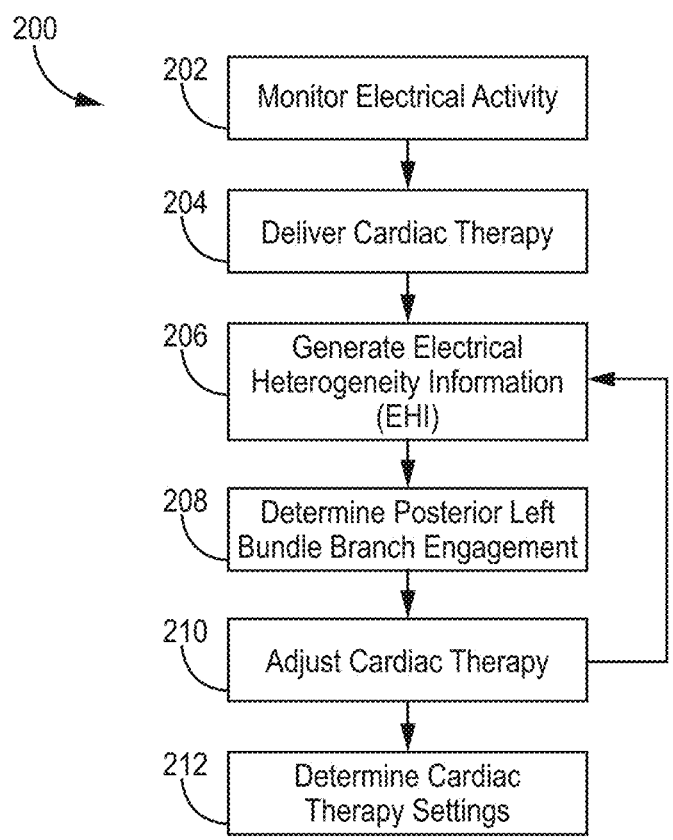
FIG. 4 is a block diagram of an illustrative method of evaluation of engagement of posterior left bundle branch by cardiac therapy and adjustment of such cardiac therapy.

An illustrative method 200 of evaluation of posterior left bundle branch engagement and adjustment of cardiac therapy is depicted in FIG. 4. Generally, it may be described that the illustrative method 200 may be used to analyze external electrical activity (e.g., from the posterior torso region of the patient) during delivering of cardiac pacing therapy and use such electrical activity to determine whether or not, and further, to what degree, the cardiac therapy is resulting in posterior left bundle branch engagement.

As shown, the method 200 may include monitoring electrical activity 202. In one embodiment, the electrical activity may be measured externally from the patient. In other words, the electrical activity may be measured from tissue outside the patient's body (e.g., skin). For example, the method 200 may include monitoring, or measuring, electrical activity using a plurality of external electrodes such as, e.g., shown and described with respect to FIGS. 1-3. In one embodiment, the plurality of external electrodes may be part, or incorporated into, a vest or band that is located about a patient's torso. More specifically, the plurality of electrodes may be described as being external surface electrodes positioned in an array configured to be located proximate the skin of the torso of a patient. It may be described that when using a plurality of external electrodes, the monitoring process 202 may provide a plurality electrocardiograms (ECGs), signals representative of the depolarization and repolarization of the patient's heart, and/or a plurality of activation times. More specifically, the plurality of ECGs may, in turn, be used to generate surrogate activation times representative of the depolarization of the heart.

The electrical activity may be monitored 202 from a posterior subset of electrodes positioned about, or in proximity to, the posterior of the torso of the patient. The electrical activity, or electrical signals, captured from the posterior subset of electrodes may be representative of one or more posterior areas of the patient's heart such as the posterior fascicle or posterior left bundle branch. In one example, the posterior subset of electrodes may be positioned on the posterior and posterolateral regions of the patient's torso.

The method 200 may include delivery of cardiac therapy 204 such as cardiac pacing therapy using an implantable or non-implantable device intended to pace or deliver electrical paces to one or more areas or regions of the patient's heart. The cardiac pacing therapy may include, but not be limited to, ventricle from atrium (VfA) pacing therapy, left ventricular basal-septal pacing therapy, His bundle pacing therapy, and intraseptal left ventricular endocardial pacing therapy.

VfA pacing therapy is further described and shown herein with respect to FIGS. 7-10. The VfA pacing therapy may be configured to deliver electrical paces to one or more areas of the cardiac conduction system including, but not limited to, areas of the left bundle branches and the right bundle branches, one or more areas of the left ventricle, one or more areas of the right atrium, etc.

Another example of cardiac conduction system pacing therapy may be His bundle pacing therapy as, e.g., described in U.S. patent application Ser. No. 16/163,132 filed Oct. 17, 2018, entitled "His Bundle and Bundle Branch Pacing Adjustment," which is incorporated herein by reference in its entirety. Still another example of cardiac conduction system pacing therapy may be intraseptal left ventricular endocardial pacing therapy as, e.g., described in U.S. Pat. No. 7,177,704 issued on Feb. 13, 2007, entitled "Pacing Method and Apparatus," which is incorporated herein by reference in its entirety.

During the delivery of the cardiac pacing therapy 204, the electrical activity may continue to be monitored 202, and may be used to generate electrical heterogeneity information (EHI) 206. The EHI (e.g., data) may be defined as information indicative of at least one of mechanical synchrony or dyssynchrony of the heart and/or electrical synchrony or dyssynchrony of the heart. In other words, EHI may represent a surrogate of actual mechanical and/or electrical functionality of a patient's heart. In at least one embodiment, relative changes in EHI (e.g., from baseline heterogeneity information to therapy heterogeneity information, from a first set of heterogeneity information to a second set of therapy heterogeneity information, etc.) may be used to determine a surrogate value representative of the changes in hemodynamic response (e.g., acute changes in LV pressure gradients). Left ventricular pressure may be typically monitored invasively with a pressure sensor located in the left ventricular of a patient's heart. As such, the use of EHI to determine a surrogate value representative of the left ventricular pressure may avoid invasive monitoring using a left ventricular pressure sensor.

In at least one embodiment, the EHI may include a standard deviation of ventricular activation times measured using some or all of the external electrodes, e.g., of the electrode apparatus 110 described herein with respect FIGS. 1-3. Further, local, or regional, EHI may include standard deviations and/or averages of activation times measured using electrodes located in certain anatomic areas of the torso. For example, external electrodes on the posterior side of the torso of a patient may be used to compute local, or regional, posterior EHI. Further, for example, external electrodes on the left side of the torso of a patient may be used to compute local, or regional, left EHI.

The EHI may be generated using one or more various systems and/or methods. For example, EHI may be generated using an array, or a plurality, of surface electrodes and/or imaging systems as described in U.S. Pat. App. Pub. No. 2012/0283587 A1 published Nov. 8, 2012 and entitled "ASSESSING INRA-CARDIAC ACTIVATION PATTERNS AND ELECTRICAL DYSSYNCHRONY," U.S. Pat. App. Pub. No. 2012/0284003 A1 published Nov. 8, 2012 and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

EHI may include one or more metrics or indices focused on, or directed to, surrogate activation times measured from the posterior and posterolateral regions of a patient's torso. For example, one of the metrics, or indices, of electrical heterogeneity may be a mean, or average, of surrogate posterior electrical activation times (MPAT) monitored by posterior electrodes positioned about the posterior and/or posterolateral regions of a patient's torso. In some examples, the MPAT may be calculated using the estimated cardiac activation times over the surface of a model heart. Another metric, or index, of electrical heterogeneity, or dyssynchrony, may be a percentage of surrogate early-activation electrical activation times (PEPA) monitored by posterior electrodes positioned about the posterior and/or posterolateral regions of a patient's torso.

The MPAT and PEPA may be determined (e.g., calculated, computed, generated, produced, etc.) from electrical activity measured only by electrodes proximate the posterior side of the patient, which may be referred to as "posterior" electrodes. The posterior electrodes may be defined as any surface electrodes located proximate the posterior side of the patient's heart, which includes the body or torso regions behind of the patient's spine. In one embodiment, the posterior electrodes may include all electrodes on the posterior of the patient. In another embodiment, the posterior electrodes may include all electrodes on the posterior of the patient and positioned between the spine of the patient and the patient's left side. In still another embodiment, the posterior electrodes may be designated based on the contour of the posterior of the heart as determined using imaging apparatus (e.g., x-ray, fluoroscopy, etc.), which may be projected to various corresponding surface electrodes positioned about the torso of the patient.

The illustrative method 200 may further include determining posterior left bundle branch engagement 208 based on the generated EHI such as one or both of MPAT and PEPA. For example, the generated EHI may be analyzed to determine the degree of posterior left bundle branch engagement.

In one embodiment, the degree of posterior left bundle branch engagement may range from complete posterior left bundle branch engagement to insufficient posterior left bundle branch engagement. Complete posterior left bundle branch engagement may be defined as all or substantially all of the posterior left bundle branch being engaged by the cardiac therapy. Sufficient posterior left bundle branch engagement may be defined as an amount of the posterior left bundle branch being engaged by the cardiac therapy so to provide efficient and sufficient left ventricular functionality. Partial posterior left bundle branch engagement may be defined as only a portion of the posterior left bundle branch being engaged by the cardiac therapy so to provide partially-efficient and partially-sufficient left ventricular functionality. Insufficient posterior left bundle branch engagement may be defined as only a small portion of the posterior left bundle branch being engaged by the cardiac therapy so to provide inefficient and insufficient left ventricular functionality. Thus, the method 200 may determine whether the cardiac therapy has resulted in complete posterior left bundle branch engagement, sufficient posterior left bundle branch engagement, partial posterior left bundle branch engagement, or insufficient posterior left bundle branch engagement.

In one or more embodiments, the mean of surrogate posterior electrical activation times monitored by the posterior electrodes (MPAT) may be used to evaluate posterior left bundle branch engagement. The MPAT may be compared against one or more thresholds or ranges to determine the degree to which the posterior left bundle branch is engaged. For example, if the MPAT is less than or equal to 30 milliseconds, then it may be determined that the left bundle branch is sufficiently engaged. Further, if the MPAT is greater than 30 milliseconds and less than 50 milliseconds, then it may be determined that the left bundle branch is partially engaged. Still further, for example, if the MPAT is greater than or equal to 50 milliseconds, then it may be determined that the left bundle branch is insufficiently engaged. It is to be understood that such thresholds and ranges in this embodiment are only one example, and other similar thresholds and ranges are contemplated by the present disclosure.

In one or more embodiments, the percentage of surrogate early-activation electrical activation times monitored by the posterior electrodes (PEPA) may be used to evaluate posterior left bundle branch engagement. To determine whether a posterior electrode, or activation monitored by the posterior electrode, constitutes early activation, the activation time may be compared to an early-activation threshold. Electrodes measuring activation times that are less than or equal to the early-activation threshold may be indicated as electrodes having early activation while electrodes measuring activation times that are greater than the early-activation threshold may be indicated as electrodes not having early activation. The early-activation threshold may be between about 15 milliseconds and about 50 milliseconds. In one embodiment, the early-activation threshold is 35 milliseconds. In other embodiments, the early-activation threshold may be greater than or equal to about 15 milliseconds, greater than or equal to about 25 milliseconds, and greater than or equal to about 30 milliseconds and/or less than or equal to about 50 milliseconds and less than or equal to about 40 milliseconds.

Thus, the early-activation electrodes, as determined by the early-activation threshold, may be divided by the total amount of posterior electrodes to provide the PEPA, and then the PEPA may be used to determine the degree of posterior left bundle branch engagement. For example, if the PEPA is greater than 75%, then it may be determined that the left bundle branch is sufficiently engaged. Further, for example, if the PEPA is greater than or equal to 50% and less than or equal to 75%, then it may be determined that the left bundle branch is partially engaged. Still further, for example, if the PEPA is less than 50%, then it may be determined that the left bundle branch is insufficiently engaged.

Figure 5A:
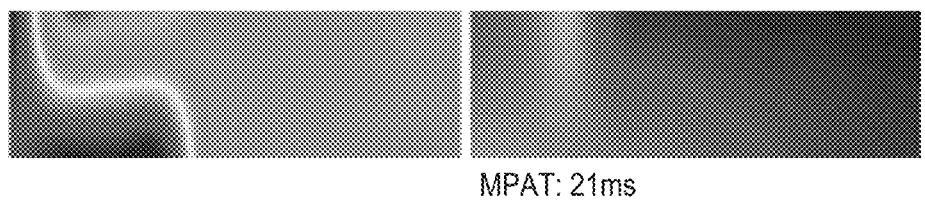
FIG. 5A depicts illustrative anterior and posterior electrical activation maps depicting sufficient posterior left bundle branch engagement.
Figure 5B:
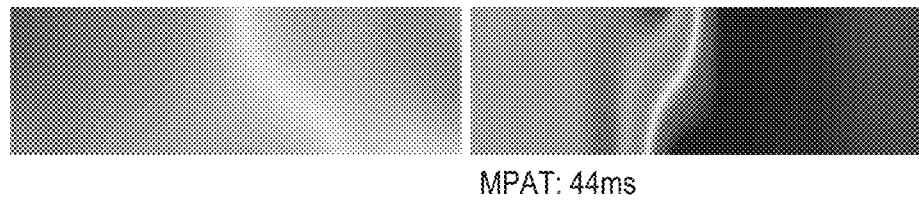
FIG. 5B depicts illustrative anterior and posterior electrical activation maps depicting partial posterior left bundle branch engagement.
Figure 5C:
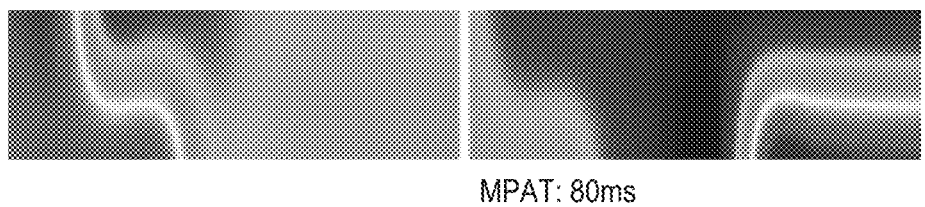
FIG. 5C depicts illustrative anterior and posterior electrical activation maps depicting insufficient posterior left bundle branch engagement.

Anterior and posterior electrical activation maps depicting sufficient posterior left bundle branch engagement are depicted in FIG. 5A, anterior and posterior electrical activation maps depicting partial posterior left bundle branch engagement are depicted in FIG. 5B, and anterior and posterior electrical activation maps depicting insufficient posterior left bundle branch engagement are depicted in FIG. 5C. Each figure includes an anterior activation map on the left, a posterior activation map on the right, and posterior EHI, namely MPAT, depicted below each posterior map.

As shown in FIG. 5A, the posterior map shows homogenous, early activation and the associated MPAT, i.e., 21 milliseconds (ms), is less than 30 ms, which indicates sufficient posterior left bundle branch engagement. As shown in FIG. 5B, the posterior map shows partial early activation and the associated MPAT, i.e., 44 ms, is less than 50 ms but greater than 30 ms, which indicates partial posterior left bundle branch engagement. As shown in FIG. 5C, the posterior map shows a small amount of early activation and the associated MPAT, i.e., 80 ms, is greater than 50 ms, which indicates insufficient posterior left bundle branch engagement.

Figure 6A:
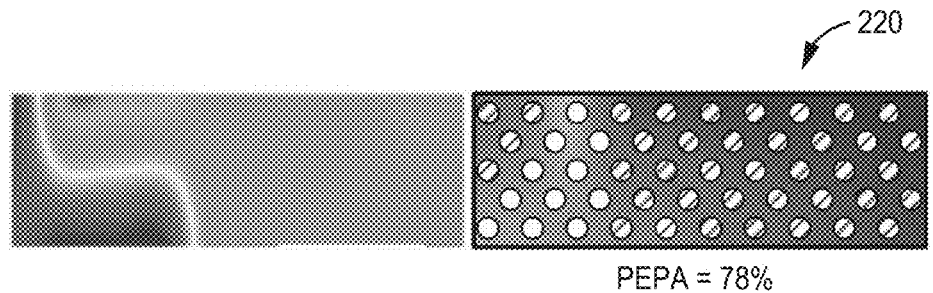
FIG. 6A depicts illustrative anterior and posterior electrical activation maps including electrode representations and depicting sufficient posterior left bundle branch engagement.
Figure 6B:
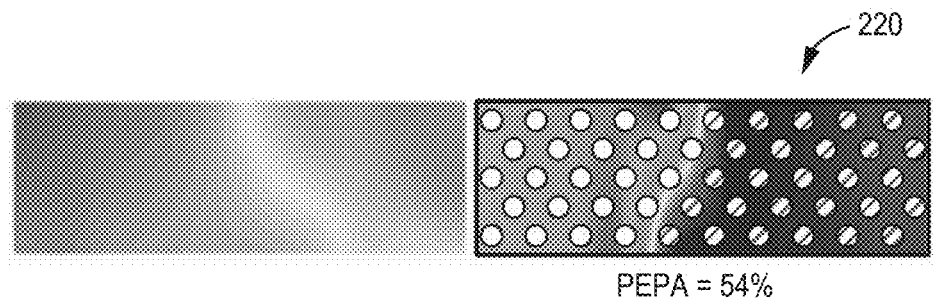
FIG. 6B depicts illustrative anterior and posterior electrical activation maps including electrode representations and depicting partial posterior left bundle branch engagement.
Figure 6C:
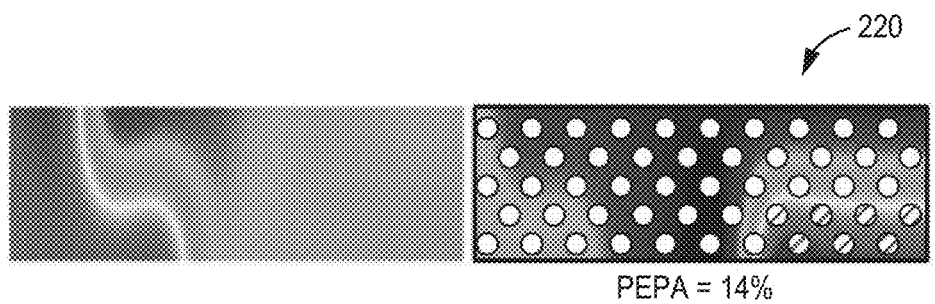
FIG. 6C depicts illustrative anterior and posterior electrical activation maps including electrode representations and depicting insufficient posterior left bundle branch engagement.

The same anterior and posterior electrical activation maps are depicted in FIGS. 6A-6C. These maps, however, also include electrode representations 220 overlaid over the posterior electrical activation maps indicating the relative location of the corresponding electrode's position about the posterior torso region of the patient. An electrode having measured early activation less than an illustrative early-activation threshold of 35 ms is represented by a circle with crosshatching (e.g., cross-hatched fill), and an electrode having measured early activation greater than or equal to the illustrative early-activation threshold of 35 ms is represented by a circle with no crosshatching (e.g., no fill).

Further, each figure includes posterior EHI, namely PEPA, depicted below each posterior map, that, as described herein, is the percentage of electrodes having early activation. As the electrodes are graphically depicted by the electrode representations 220, the PEPA may be described as the cross-hatched electrode representations 220 divided by the total number of posterior electrodes. As shown in FIG. 6A, the posterior map shows homogenous, early activation and the associated PEPA, i.e., 78% (39 of 50 electrodes), is greater than 75%, which indicates sufficient posterior left bundle branch engagement. As shown in FIG. 5B, the posterior map shows partial early activation and the associated PEPA, i.e., 54% (27 of 50 electrodes), is less than 75% but greater than 50%, which indicates partial posterior left bundle branch engagement. As shown in FIG. 5C, the posterior map shows a small amount of early activation and the associated PEPA, i.e., 14% (7 of 50 electrodes), is less 50%, which indicates insufficient posterior left bundle branch engagement.

One or more posterior EHI metrics may be used in conjunction, or together, to determine posterior left bundle branch engagement. In one embodiment, MPAT may be used with PEPA to determine posterior left bundle branch engagement. For example, if the PEPA is greater than 75% and MPAT is less than or equal to 30 milliseconds, then it may be determined that the left bundle branch is sufficiently engaged. Further, for example, if the PEPA is greater than or equal to 50% and less than or equal to 75% and MPAT is greater than 30 milliseconds and less than 50 milliseconds, then it may be determined that the left bundle branch is partially engaged. Still further, for example, if either of PEPA is less than 50% and MPAT is greater than or equal to 50 milliseconds, then it may be determined that the left bundle branch is insufficiently engaged.

After the illustrative method 200 has determined posterior left bundle branch engagement 208, the method 200 may further including adjusting, or modifying, the cardiac therapy 210 to, for example, increase the posterior left bundle branch engagement in an effort to provide more effective heart functionality. It is to be understood that posterior left bundle branch engagement may be only one factor to consider when adjusting cardiac therapy, and thus, the cardiac therapy adjustment described with respect to engagement of the posterior left bundle branch may be utilized in conjunction with other factors not described herein.

The method 200 may adjust the cardiac pacing therapy 208 in various ways. For example, the cardiac pacing therapy may include, or define, a plurality of different pacing settings, or parameters, that may be adjusted. The plurality of pacing settings may include, but not be limited to, pacing electrode location, pacing electrode angle, pacing amplitude or power, pacing times such as A-V delay, V-V delay, and pacing pulse length, use of one or more pacing electrodes, and/or use of one or more pacing vectors. In other words, one or more of the pacing settings may be changed (e.g., increase, decreased, moved, etc.) during adjustment of the cardiac pacing therapy 208.

After adjusting the cardiac pacing therapy 208, the method 200 may return to generating EHI 206 from the electrical activity monitored during the newly-adjusted cardiac pacing therapy. Then, the method 200 may again adjust the cardiac pacing therapy 210, generate EHI 206, determine posterior left bundle branch engagement 208, and continue looping until a plurality of different cardiac pacing therapy configurations, each having at least one different pacing parameter, have been attempted. In one embodiment, the pacing settings may be adjusted incrementally by steps or percentages in a way that "sweeps" across a range of possible parameters for each particular setting. For example, A-V delay may start at a level equal to 70% of patient's intrinsic A-V delay and may be progressively decreased in steps of about 10 ms to about 20 ms until a predefined minimum of 60 ms. Additionally, for example, the paced setting may be location or angle of the pacing electrode, and the location or angle of the pacing electrode may be adjusted incrementally by an implanter to provide a range of different locations and angles.

It may be described that processes 206, 208, 210 define a "closed-loop." For example, processes 206, 208, 2010 may continue looping for a plurality of different pacing settings or configurations, and for each of the plurality of different pacing settings or configurations, EHI information may be generated 206 and posterior left bundle branch engagement may be determined 208. The EHI generated for the plurality of different pacing settings or configurations, and in turn, the determinization of posterior left bundle branch engagement may then be used to determine selected pacing settings of the cardiac pacing therapy 212. The selected pacing settings for the cardiac conduction therapy may, in some embodiments, be referred to as the "optimal" pacing settings as, for example, the pacing settings providing the most complete posterior left bundle branch engagement may be selected. It is to be understood, however, the pacing settings providing the most complete posterior left bundle branch engagement may not necessarily be the pacing settings that would be selected as considerations other than posterior left bundle branch engagement exist such as, for example, battery life of the device performing the therapy. Thus, the selected, or optimal, pacing settings for the cardiac pacing therapy may represent a balance of many factors including posterior left bundle branch engagement.

For example, MPAT may be utilized to determine the selected pacing settings for the cardiac pacing therapy 212. As such, a plurality of different pacing settings may be utilized 210, and an MPAT may be generated for each of the plurality of different pacing settings 2018. In this example, the lowest MPAT may be indicative of the most complete posterior left bundle branch engagement for the cardiac pacing therapy, and thus, the cardiac pacing therapy settings having, or corresponding to, the lowest MPAT may be selected 212 to be used with the cardiac pacing therapy.

Further illustrative systems, methods, and processes for optimizing the cardiac pacing therapy may be described in U.S. patent application Ser. No. 15/934,517 filed on Mar. 23, 2019 entitled "Evaluation of Ventricle from Atrium Pacing Therapy" and U.S. Prov. Pat. App. Ser. No. 62/725,763 filed on Aug. 31, 2018 entitled "Adaptive VFA Cardiac Therapy," each of which is incorporated herein by reference in its entirety.

Figure 7:
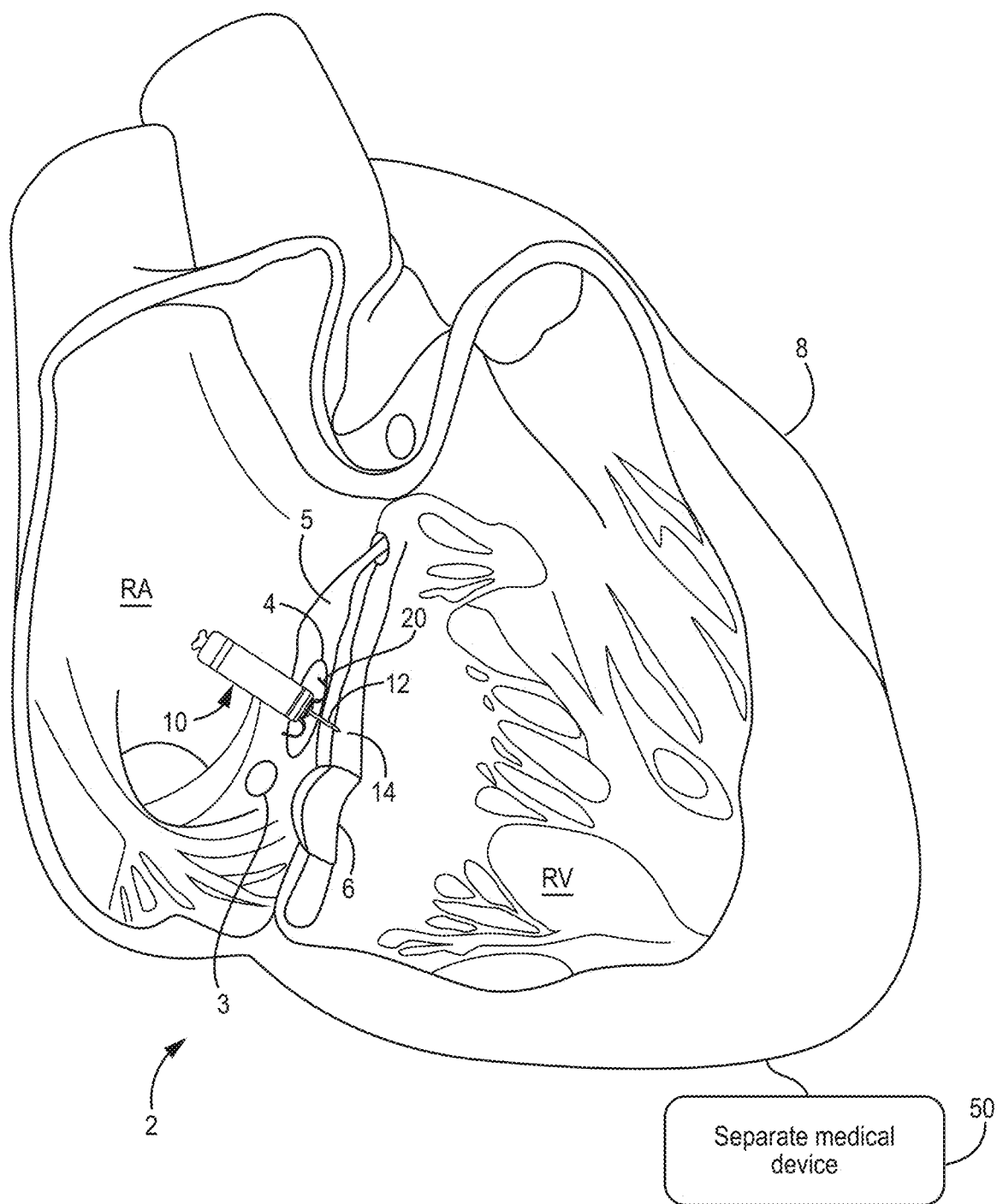
FIG. 7 is a conceptual diagram of an illustrative cardiac therapy system including an intracardiac medical device implanted in a patient's heart and a separate medical device positioned outside of the patient's heart.

An illustrative ventricle from atrium (VfA) cardiac therapy system is depicted in FIG. 7 that may be configured to be used with, for example, the systems and methods described herein with respect to FIGS. 1-6. Although it is to be understood that the present disclosure may utilize one or both of leadless and leaded implantable medical devices, the illustrative cardiac therapy system of FIG. 7 includes a leadless intracardiac medical device 10 that may be configured for single or dual chamber therapy and implanted in a patient's heart 8. In some embodiments, the device 10 may be configured for single chamber pacing and may, for example, switch between single chamber and multiple chamber pacing (e.g., dual or triple chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device 10 against the atrial endocardium in a target implant region 4. The target implant region 4 may lie between the Bundle of His 5 and the coronary sinus 3 and may be adjacent, or next to, the tricuspid valve 6. The device 10 may be described as a ventricle-from-atrium device because, for example, the device 10 may perform, or execute, one or both of sensing electrical activity from and providing therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal and/or septal region of the left ventricular myocardium of the patient's heart from the triangle of Koch region of the right atrium through the right atrial endocardium and central fibrous body.

The device 10 may be described as a leadless implantable medical device. As used herein, "leadless" refers to a device being free of a lead extending out of the patient's heart 8. Further, although a leadless device may have a lead, the lead would not extend from outside of the patient's heart to inside of the patient's heart or would not extend from inside of the patient's heart to outside of the patient's heart. Some leadless devices may be introduced through a vein, but once implanted, the device is free of, or may not include, any transvenous lead and may be configured to provide cardiac therapy without using any transvenous lead. Further, a leadless VfA device, in particular, does not use a lead to operably connect to an electrode in the ventricle when a housing of the device is positioned in the atrium. Additionally, a leadless electrode may be coupled to the housing of the medical device without using a lead between the electrode and the housing.

The device 10 may include a dart electrode assembly 12 defining, or having, a straight shaft extending from a distal end region of device 10. The dart electrode assembly 12 may be placed, or at least configured to be placed, through the atrial myocardium and the central fibrous body and into the ventricular myocardium 14, or along the ventricular septum, without perforating entirely through the ventricular endocardial or epicardial surfaces. The dart electrode assembly 12 may carry, or include, an electrode at a distal end region of the shaft such that the electrode may be positioned within the ventricular myocardium for sensing ventricular signals and delivering ventricular pacing pulses (e.g., to depolarize the left ventricle and/or right ventricle to initiate a contraction of the left ventricle and/or right ventricle). In some examples, the electrode at the distal end region of the shaft is a cathode electrode provided for use in a bipolar electrode pair for pacing and sensing. While the implant region 4 as illustrated may enable one or more electrodes of the dart electrode assembly 12 to be positioned in the ventricular myocardium, it is recognized that a device having the aspects disclosed herein may be implanted at other locations for multiple chamber pacing (e.g., dual or triple chamber pacing), single chamber pacing with multiple chamber sensing, single chamber pacing and/or sensing, or other clinical therapy and applications as appropriate.

It is to be understood that although device 10 is described herein as including a single dart electrode assembly, the device 10 may include more than one dart electrode assembly placed, or configured to be placed, through the atrial myocardium and the central fibrous body, and into the ventricular myocardium 14, or along the ventricular septum, without perforating entirely through the ventricular endocardial or epicardial surfaces. Additionally, each dart electrode assembly may carry, or include, more than a single electrode at the distal end region, or along other regions (e.g., proximal or central regions), of the shaft.

The cardiac therapy system 2 may also include a separate medical device 50 (depicted diagrammatically in FIG. 7), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead including, or carrying, a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy (e.g., defibrillation shocks provided by the defibrillation electrode of the defibrillation lead), the separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may further include a sensing circuit. The sensing circuit may be configured to obtain electrical signals sensed via one or more combinations of electrodes and to process the obtained signals. The components of the sensing circuit may include analog components, digital components, or a combination thereof. The sensing circuit may, for example, include one or more sense amplifiers, filters, rectifiers, threshold detectors, analog-to-digital converters (ADCs), or the like. The sensing circuit may convert the sensed signals to digital form and provide the digital signals to the control circuit for processing and/or analysis. For example, the sensing circuit may amplify signals from sensing electrodes and convert the amplified signals to multi-bit digital signals by an ADC, and then provide the digital signals to the control circuit. In one or more embodiments, the sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical-pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 8:
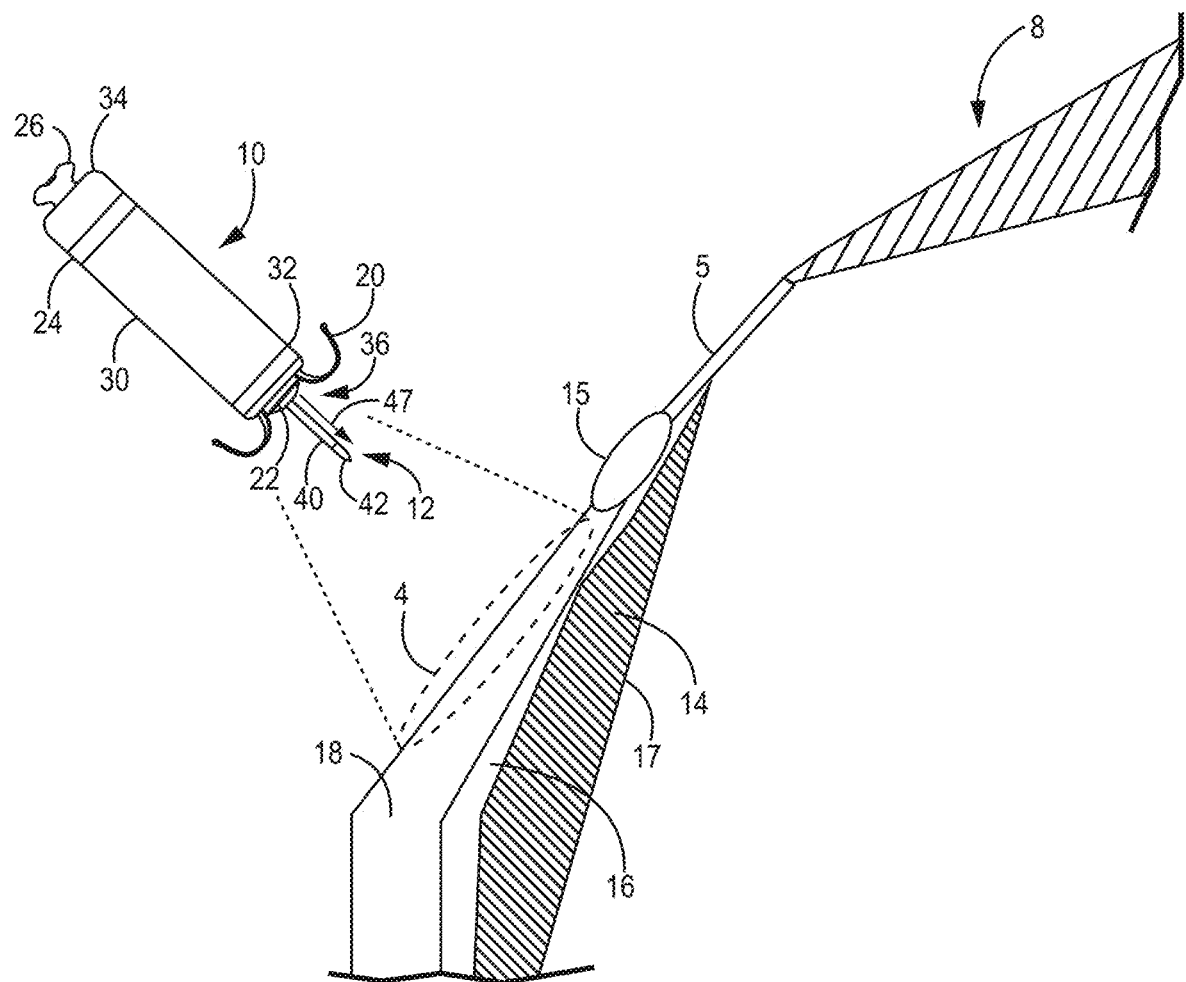
FIG. 8 is an enlarged conceptual diagram of the intracardiac medical device of FIG. 7 and anatomical structures of the patient's heart.

FIG. 8 is an enlarged conceptual diagram of the intracardiac medical device 10 of FIG. 7 and anatomical structures of the patient's heart 8. In particular, the device 10 is configured to sense cardiac signals and/or deliver pacing therapy. The intracardiac device 10 may include a housing 30. The housing 30 may define a hermetically-sealed internal cavity in which internal components of the device 10 reside, such as a sensing circuit, therapy delivery circuit, control circuit, memory, telemetry circuit, other optional sensors, and a power source as generally described in conjunction with FIG. 10. The housing 30 may include (e.g., be formed of or from) an electrically conductive material such as, e.g., titanium or titanium alloy, stainless steel, MP35N (a non-magnetic nickel-cobalt-chromium-molybdenum alloy), platinum alloy, or other bio-compatible metal or metal alloy. In other examples, the housing 30 may include (e.g., be formed of or from) a non-conductive material including ceramic, glass, sapphire, silicone, polyurethane, epoxy, acetyl co-polymer plastics, polyether ether ketone (PEEK), a liquid crystal polymer, or other biocompatible polymer.

In at least one embodiment, the housing 30 may be described as extending between a distal end region 32 and a proximal end region 34 and as defining a generally-cylindrical shape, e.g., to facilitate catheter delivery. In other embodiments, the housing 30 may be prismatic or any other shape to perform the functionality and utility described herein. The housing 30 may include a delivery tool interface member 26, e.g., defined, or positioned, at the proximal end region 34, for engaging with a delivery tool during implantation of the device 10.

All or a portion of the housing 30 may function as a sensing and/or pacing electrode during cardiac therapy. In the example shown, the housing 30 includes a proximal housing-based electrode 24 that circumscribes a proximal portion (e.g., closer to the proximal end region 34 than the distal end region 32) of the housing 30. When the housing 30 is (e.g., defines, formed from, etc.) an electrically-conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to form, or define, the proximal housing-based electrode 24. When the housing 30 is (e.g., defines, formed from, etc.) a non-conductive material, such as a ceramic, glass or polymer material, an electrically-conductive coating or layer, such as a titanium, platinum, stainless steel, or alloys thereof, may be applied to one or more discrete areas of the housing 30 to form, or define, the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32, and therefore, may be referred to as a proximal housing-based electrode 24. In other examples, however, the proximal housing-based electrode 24 may be located at other positions along the housing 30, e.g., more distal relative to the position shown.

At the distal end region 32, the device 10 may include a distal fixation and electrode assembly 36, which may include one or more fixation members 20 and one or more dart electrode assemblies 12 of equal or unequal length. In one such example as shown, a single dart electrode assembly 12 includes a shaft 40 extending distally away from the housing distal end region 32 and one or more electrode elements, such as a tip electrode 42 at or near the free, distal end region of the shaft 40. The tip electrode 42 may have a conical or hemi-spherical distal tip with a relatively narrow tip-diameter (e.g., less than about 1 millimeter (mm)) for penetrating into and through tissue layers without using a sharpened tip or needle-like tip having sharpened or beveled edges.

The dart electrode assembly 12 may be configured to pierce through one or more tissue layers to position the tip electrode 42 within a desired tissue layer such as, e.g., the ventricular myocardium. As such, the height 47, or length, of the shaft 40 may correspond to the expected pacing site depth, and the shaft 40 may have a relatively-high compressive strength along its longitudinal axis to resist bending in a lateral or radial direction when pressed against and into the implant region 4. If a second dart electrode assembly 12 is employed, its length may be unequal to the expected pacing site depth and may be configured to act as an indifferent electrode for delivering of pacing energy to and/or sensing signals from the tissue. In one embodiment, a longitudinal axial force may be applied against the tip electrode 42, e.g., by applying longitudinal pushing force to the proximal end 34 of the housing 30, to advance the dart electrode assembly 12 into the tissue within the target implant region.

The shaft 40 may be described as longitudinally non-compressive and/or elastically deformable in lateral or radial directions when subjected to lateral or radial forces to allow temporary flexing, e.g., with tissue motion, but may return to its normally straight position when lateral forces diminish. Thus, the dart electrode assembly 12 including the shaft 40 may be described as being resilient. When the shaft 40 is not exposed to any external force, or to only a force along its longitudinal central axis, the shaft 40 may retain a straight, linear position as shown.

In other words, the shaft 40 of the dart electrode assembly 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by a height, or length, 47 of the shaft 40.

The one or more fixation members 20 may be described as one or more "tines" having a normally curved position. The tines may be held in a distally extended position within a delivery tool. The distal tips of tines may penetrate the heart tissue to a limited depth before elastically, or resiliently, curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual or triple chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode assembly 12 may at least partially define the height 47, or length, of the shaft 40 for penetrating through the atrial endocardium 18 in the target implant region 4, through the central fibrous body 16, and into the ventricular myocardium 14 without perforating through the ventricular endocardial surface 17. When the height 47, or length, of the dart electrode assembly 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode assembly 12 may have a total combined height 47, or length, of tip electrode 42 and shaft 40 from about 3 mm to about 8 mm in various examples. The diameter of the shaft 40 may be less than about 2 mm, and may be about 1 mm or less, or even about 0.6 mm or less.

Figure 9:
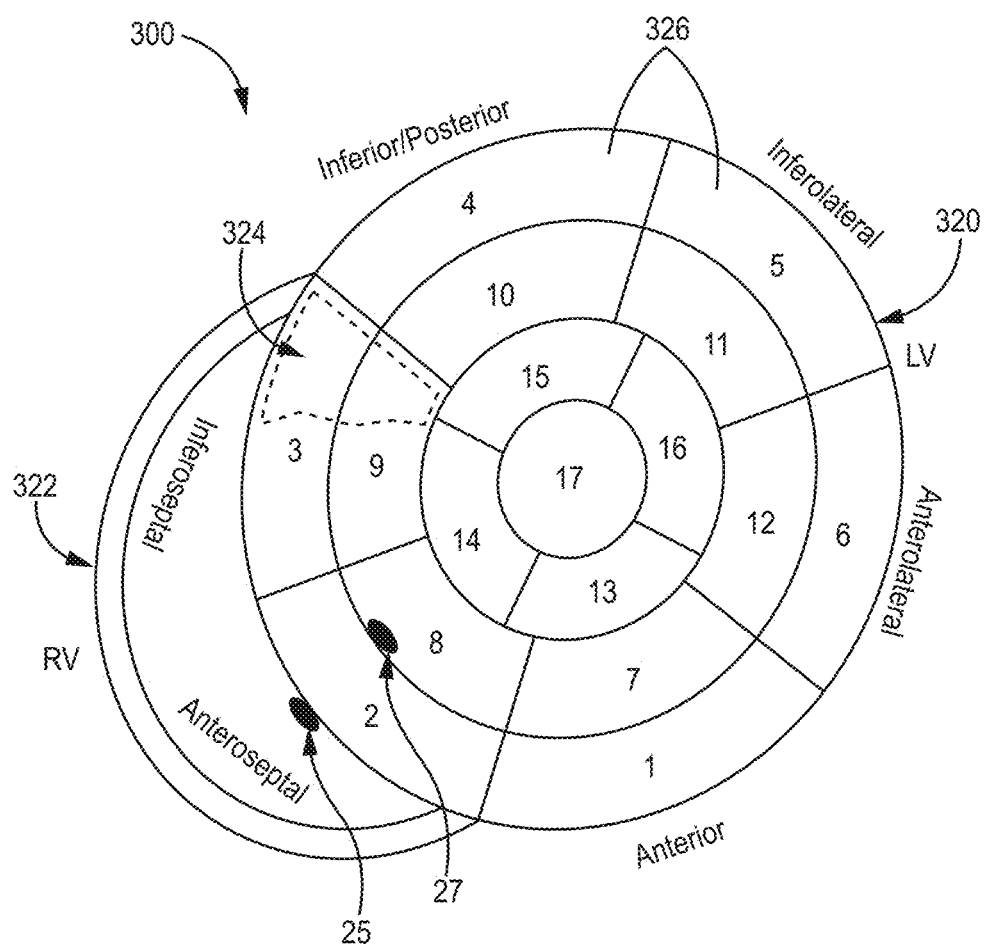
FIG. 9 is a conceptual diagram of a map of a patient's heart in a standard 17 segment view of the left ventricle showing various electrode implantation locations for use with the illustrative systems and devices described herein.

FIG. 9 is a two-dimensional (2D) ventricular map 300 of a patient's heart (e.g., a top-down view) showing the left ventricle 320 in a standard 17 segment view and the right ventricle 322. The map 300 defines, or includes, a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) 25 and left bundle branch (LBB) 27.

In some embodiments, any of the tissue-piercing electrodes of the present disclosure may be implanted in the basal and/or septal region of the left ventricular myocardium of the patient's heart. In particular, the tissue-piercing electrode may be implanted from the triangle of Koch region of the right atrium through the right atrial endocardium and central fibrous body. Once implanted, the tissue-piercing electrode may be positioned in the target implant region 4 (FIGS. 7-8), such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal inferoseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of one or more of the basal inferoseptal area 3 and mid-inferoseptal area 9 (e.g., the basal inferoseptal area only, the mid-inferoseptal area only, or both the basal inferoseptal area and the mid-inferoseptal area). For example, the high inferior/posterior basal septal region may include region 324 illustrated generally as a dashed-line boundary. As shown, the dashed line boundary represents an approximation of where the high inferior/posterior basal septal region is located, which may take a somewhat different shape or size depending on the particular application.

Figure 10:
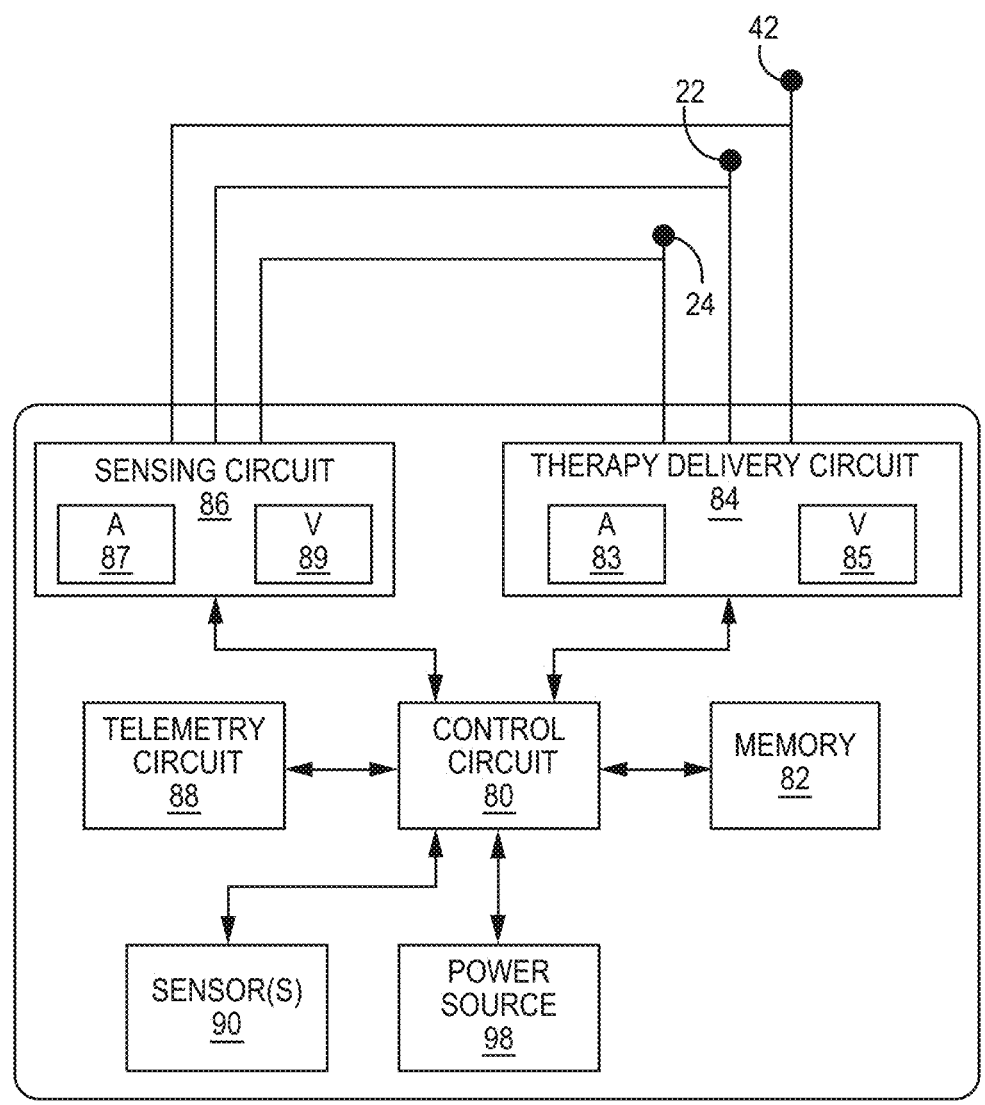
FIG. 10 is a block diagram of illustrative circuitry that may be enclosed within the housing of the medical devices of FIGS. 7-8, for example, to provide the functionality and therapy described herein.

A block diagram of circuitry is depicted in FIG. 10 that may be enclosed within the housings 30 of the device 10 to provide the functions of sensing cardiac signals, determining capture, and/or delivering pacing therapy according to one example or within the housings of any other medical devices described herein. The separate medical device 50 as shown in FIG. 7 may include some or all the same components, which may be configured in a similar manner. The electronic circuitry enclosed within the housing 30 may include software, firmware, and hardware that cooperatively monitor atrial and ventricular electrical cardiac signals, determine whether cardiac system capture has occurred, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing signals that are correlated to one or more physiological functions, states, or conditions of the patient. For example, the sensor(s) 90 may include a patient activity sensor, for use in determining a need for pacing therapy and/or controlling a pacing rate. In other words, the device 10 may include other sensors 90 for sensing signals from the patient for use in determining whether to deliver and/or controlling electrical stimulation therapies delivered by the therapy delivery circuit 84.

The power source 98 may provide power to the circuitry of the device 10 including each of the components 80, 82, 84, 86, 88, 90 as needed. The power source 98 may include one or more energy storage devices, such as one or more rechargeable or non-rechargeable batteries. The connections (not shown) between the power source 98 and each of the components 80, 82, 84, 86, 88, 90 may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown in FIG. 10 represent functionality included in the device 10 and may include any discrete and/or integrated electronic circuit components that implement analog, and/or digital circuits capable of producing the functions attributed to the medical device 10 described herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer readable media storing instructions that, when executed by one or more processing circuits, cause the control circuit 80 and/or other processing circuitry to determine posterior left bundle branch engagement and/or perform a single, dual, or triple chamber calibrated pacing therapy (e.g., single or multiple chamber pacing), or other cardiac therapy functions (e.g., sensing or delivering therapy), attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (A-V) pacing interval. If an R-wave is sensed before the A-V pacing interval expires, the ventricular pacing pulse may be inhibited. If the A-V pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., P-P intervals between consecutive P-wave sensed event signals received from the atrial sensing channel 87, R-R intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrode 42 and the proximal housing-based electrode 24 may be coupled to the ventricular pacing circuit 85 as a bipolar cathode and anode pair for delivering ventricular pacing pulses, e.g., upon expiration of an A-V or V-V pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set one or more atrial pacing intervals according to a programmed lower pacing rate or a temporary lower rate set according to a rate-responsive sensor indicated pacing rate. Atrial pacing circuit may be controlled to deliver an atrial pacing pulse if the atrial pacing interval expires before a P-wave sensed event signal is received from the atrial sensing channel 87. The control circuit 80 starts an A-V pacing interval in response to a delivered atrial pacing pulse to provide synchronized multiple chamber pacing (e.g., dual or triple chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single chamber or multiple chamber pacing (e.g., dual or triple chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

The techniques described in this disclosure, including those attributed to the IMD 10, device 50, the computing apparatus 140, and the computing device 160 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

All references and publications cited herein are expressly incorporated herein by reference in their entirety for all purposes, except to the extent any aspect incorporated directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between the two elements). Either term may be modified by "operatively" and "operably," which may be used interchangeably, to describe that the coupling or connection is configured to allow the components to interact to carry out at least some functionality (for example, a first medical device may be operatively coupled to another medical device to transmit information in the form of data or to receive data therefrom).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of" and the like are subsumed in "comprising," and the like.

The term "and/or" means one or all the listed elements or a combination of at least two of the listed elements. The phrases "at least one of" "comprises at least one of" and "one or more of" followed by a list refers to any one of the items in the list and any combination of two or more items in the list.

Illustrative Embodiments

Embodiment 1: A system comprising:
electrode apparatus comprising a plurality of posterior electrodes to monitor electrical activity from a patient's posterior; and
computing apparatus comprising processing circuitry and coupled to the electrode apparatus and configured to:
monitor electrical activity of the patient's heart using the plurality of posterior electrodes during delivery of cardiac therapy,
generate electrical heterogeneity information (EHI) based on the monitored electrical activity during delivery of cardiac therapy, and
determine a degree of posterior left bundle branch engagement based on the generated EHI.

Embodiment 2: A method comprising:
monitoring electrical activity of the patient's heart using a plurality of posterior electrodes from a patient's posterior during delivery of cardiac therapy;
generating electrical heterogeneity information (EHI) based on the monitored electrical activity during delivery of cardiac therapy; and
determining a degree of posterior left bundle branch engagement based on the generated EHI.

Embodiment 3: The system or method as set forth in one of embodiments 1-2, wherein generating EHI based on the monitored electrical activity during delivery of cardiac therapy comprises generating a mean of surrogate posterior electrical activation times monitored by the posterior electrodes.

Embodiment 4: The system or method as set forth in one of embodiments 1-3, wherein determining a degree of posterior left bundle branch engagement based on the generated EHI comprises determining that left bundle branch is sufficiently engaged if the mean of surrogate posterior electrical activation times monitored by the posterior electrodes is less than or equal to 30 milliseconds, intermediately-engaged if the mean of surrogate posterior electrical activation times monitored by the posterior electrodes is greater than 30 milliseconds and less than 50 milliseconds, or insufficiently-engaged if the mean of surrogate posterior electrical activation times monitored by the posterior electrodes is greater than or equal to 50 milliseconds.

Embodiment 5: The system or method as set forth in one of embodiments 1-4, wherein generating EHI based on the monitored electrical activity during delivery of cardiac therapy comprises generating a percentage of surrogate early-activation electrical activation times monitored by the posterior electrodes that is less than an early-activation threshold.

Embodiment 6: The system or method as set forth in embodiment 5, wherein the early-activation threshold is 35 milliseconds.

Embodiment 7: The system or method as set forth in one of embodiments 5-6, wherein determining a degree of posterior left bundle branch engagement based on the generated EHI comprises determining that left bundle branch is sufficiently engaged if the percentage of surrogate early-activation electrical activation times is greater than 75%, intermediately-engaged if the percentage of surrogate early-activation electrical activation times is greater than or equal to 50% and less than or equal to 75%, or insufficiently-engaged if the percentage of surrogate early-activation electrical activation times is less than 50%.

Embodiment 8: The system or method as set forth in one of embodiments 1-7, wherein the cardiac therapy is ventricle-from-atrium (VfA) pacing therapy.

Embodiment 9: The system or method as set forth in one of embodiments 1-8, wherein the computing apparatus is further configured to execute or the method further comprises adjusting the cardiac therapy to increase the degree of posterior left bundle branch engagement.

Embodiment 10: A system comprising:
electrode apparatus comprising a plurality of posterior electrodes to monitor electrical activity from a patient's posterior; and
computing apparatus comprising processing circuitry and coupled to the electrode apparatus and configured to:
monitor electrical activity of the patient's heart using the plurality of posterior electrodes during delivery of cardiac pacing therapy,
determine a degree of posterior left bundle branch engagement based on the monitored electrical activity, and
adjust one or more pacing settings of the cardiac pacing therapy based on the determined degree of left bunch branch engagement.

Embodiment 11: The system as set forth in embodiment 10, wherein the cardiac pacing therapy comprises one or more of ventricle-from-atrium (VfA) pacing therapy, His bundle pacing therapy, and intraseptal left ventricular endocardial pacing.

Embodiment 12: The system or method as set forth in one of embodiments 1-11, wherein the plurality of posterior electrodes comprises a plurality of surface electrodes positioned in an array to be located proximate skin of a torso of the patient's posterior.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A system comprising:
an electrode apparatus comprising a plurality of posterior electrodes to monitor electrical activity from a posterior of a patient's torso; and
a computing apparatus comprising processing circuitry and coupled to the electrode apparatus and configured to:
monitor electrical activity of the patient's heart using the plurality of posterior electrodes during delivery of cardiac therapy,
generate electrical heterogeneity information (EHI) based on the monitored electrical activity during delivery of cardiac therapy, wherein generating EHI based on the monitored electrical activity during delivery of cardiac therapy comprises generating a mean of posterior electrical activation times monitored by the posterior electrodes, and
determine a degree of posterior left bundle branch engagement by the cardiac therapy based on the generated EHI, wherein determining a degree of posterior left bundle branch engagement based on the generated EHI comprises determining that left bundle branch is sufficiently engaged if the mean of posterior electrical activation times monitored by the posterior electrodes is less than or equal to 30 milliseconds, intermediately-engaged if the mean of posterior electrical activation times monitored by the posterior electrodes is greater than 30 milliseconds and less than 50 milliseconds, or insufficiently-engaged if the mean of posterior electrical activation times monitored by the posterior electrodes is greater than or equal to 50 milliseconds.

2. The system of claim 1, wherein generating EHI based on the monitored electrical activity during delivery of cardiac therapy comprises generating a percentage of early-activation electrical activation times monitored by the posterior electrodes that is less than an early-activation threshold.

3. The system of claim 2, wherein the early-activation threshold is 35 milliseconds.

4. The system of claim 2, wherein determining a degree of posterior left bundle branch engagement based on the generated EHI comprises determining that left bundle branch is sufficiently engaged if the percentage of early-activation electrical activation times is greater than 75%, intermediately-engaged if the percentage of early-activation electrical activation times is greater than or equal to 50% and less than or equal to 75%, or insufficiently-engaged if the percentage of early-activation electrical activation times is less than 50%.

5. The system of claim 1, wherein the cardiac therapy is ventricle-from-atrium (VfA) pacing therapy.

6. The system of claim 1, wherein the computing apparatus is further configured to adjust the cardiac therapy to increase the degree of posterior left bundle branch engagement.

7. The system of claim 1, wherein the plurality of posterior electrodes comprises a plurality of surface electrodes positioned in an array to be attached to the patient's skin.

8. A method comprising:
monitoring electrical activity of the patient's heart using a plurality of posterior electrodes from a posterior of a patient's torso during delivery of cardiac therapy;
generating electrical heterogeneity information (EHI) based on the monitored electrical activity during delivery of cardiac therapy, wherein generating EHI based on the monitored electrical activity during delivery of cardiac therapy comprises generating a mean of posterior electrical activation times monitored by the posterior electrodes; and
determining a degree of posterior left bundle branch engagement by the cardiac therapy based on the generated EHI, wherein determining a degree of posterior left bundle branch engagement based on the generated EHI comprises determining that left bundle branch is sufficiently engaged if the mean of posterior electrical activation times monitored by the posterior electrodes is less than or equal to 30 milliseconds, intermediately-engaged if the mean of posterior electrical activation times monitored by the posterior electrodes is greater than 30 milliseconds and less than 50 milliseconds, or insufficiently-engaged if the mean of posterior electrical activation times monitored by the posterior electrodes is greater than or equal to 50 milliseconds.

9. The method of claim 8, wherein generating EHI based on the monitored electrical activity during delivery of cardiac therapy comprises generating a percentage of early-activation electrical activation times monitored by the posterior electrodes that is less than an early-activation threshold.

10. The method of claim 9, wherein the early-activation threshold is 35 milliseconds.

11. The method of claim 9, wherein determining a degree of posterior left bundle branch engagement based on the generated EHI comprises determining that left bundle branch is sufficiently engaged if the percentage of early-activation electrical activation times is greater than 75%, intermediately-engaged if the percentage of surrogate early-activation electrical activation times is greater than or equal to 50% and less than or equal to 75%, or insufficiently-engaged if the percentage of surrogate early-activation electrical activation times is less than 50%.

12. The method of claim 8, wherein the cardiac therapy is ventricle-from-atrium (VfA) pacing therapy.

13. The method of claim 8, the method further comprising adjusting the cardiac therapy to increase the degree of posterior left bundle branch engagement.

14. The method of claim 8, wherein the plurality of posterior electrodes comprises a plurality of surface electrodes positioned in an array to be attached to the patient's skin.

15. A system comprising:
an electrode apparatus comprising a plurality of posterior electrodes to monitor electrical activity from a posterior of a patient's torso; and
a computing apparatus comprising processing circuitry and coupled to the electrode apparatus and configured to:
monitor electrical activity of the patient's heart using the plurality of posterior electrodes during delivery of cardiac therapy,
generate electrical heterogeneity information (EHI) based on the monitored electrical activity during delivery of cardiac therapy, wherein generating EHI based on the monitored electrical activity during delivery of cardiac therapy comprises generating a percentage of early-activation electrical activation times monitored by the posterior electrodes that is less than an early-activation threshold, wherein the early-activation threshold is 35 milliseconds, and
determine a degree of posterior left bundle branch engagement by the cardiac therapy based on the generated EHI.

16. The system of claim 15, wherein the cardiac therapy is ventricle-from-atrium (VfA) pacing therapy.

17. The system of claim 15, wherein the computing apparatus is further configured to adjust the cardiac therapy to increase the degree of posterior left bundle branch engagement.

18. The system of claim 15, wherein the plurality of posterior electrodes comprises a plurality of surface electrodes positioned in an array to be attached to the patient's skin.

19. A method comprising:
monitoring electrical activity of the patient's heart using a plurality of posterior electrodes from a posterior of a patient's torso during delivery of cardiac therapy;
generating electrical heterogeneity information (EHI) based on the monitored electrical activity during delivery of cardiac therapy, wherein generating EHI based on the monitored electrical activity during delivery of cardiac therapy comprises generating a percentage of early-activation electrical activation times monitored by the posterior electrodes that is less than an early-activation threshold, wherein the early-activation threshold is 35 milliseconds; and
determining a degree of posterior left bundle branch engagement by the cardiac therapy based on the generated EHI.

20. The method of claim 19, the method further comprising adjusting the cardiac therapy to increase the degree of posterior left bundle branch engagement.

21. The method of claim 19, wherein the plurality of posterior electrodes comprises a plurality of surface electrodes positioned in an array to be attached to the patient's skin.

* * * * *